United States Patent
Masahiro et al.

(10) Patent No.: US 9,793,499 B2
(45) Date of Patent: Oct. 17, 2017

(54) ORGANIC IRIDIUM COMPLEX FOR ORGANIC ELECTROLUMINESCENT ELEMENT

(71) Applicants: Tanaka Kikinzoku Kogyo K.K., Tokyo (JP); Osaka Prefecture University Public Corporation, Osaka (JP)

(72) Inventors: Yasushi Masahiro, Tokyo (JP); Shigeyuki Yagi, Osaka (JP); Junichi Taniuchi, Ibaraki (JP)

(73) Assignees: TANAKA KIKINZOKU KOGYO K.K., Tokyo (JP); OSAKA PREFECTURE UNIVERSITY PUBLIC CORPORATION, Osaka (JP)

( * ) Notice: Subject to any disclaimer, the term of this patent is extended or adjusted under 35 U.S.C. 154(b) by 0 days.

(21) Appl. No.: 15/314,648

(22) PCT Filed: Jun. 9, 2015

(86) PCT No.: PCT/JP2015/066570
§ 371 (c)(1),
(2) Date: Nov. 29, 2016

(87) PCT Pub. No.: WO2015/190464
PCT Pub. Date: Dec. 17, 2015

(65) Prior Publication Data
US 2017/0200907 A1    Jul. 13, 2017

(30) Foreign Application Priority Data

Jun. 13, 2014 (JP) ................. 2014-121997
Mar. 9, 2015 (JP) ................. 2015-045467

(51) Int. Cl.
*C07F 15/00* (2006.01)
*H01L 51/50* (2006.01)
*H01L 51/00* (2006.01)
*C09K 11/02* (2006.01)
*C09K 11/06* (2006.01)

(52) U.S. Cl.
CPC ...... *H01L 51/0085* (2013.01); *C07F 15/0033* (2013.01); *C09K 11/025* (2013.01); *C09K 11/06* (2013.01); *C09K 2211/1007* (2013.01); *C09K 2211/1011* (2013.01); *C09K 2211/1029* (2013.01); *C09K 2211/1088* (2013.01); *C09K 2211/1092* (2013.01); *C09K 2211/185* (2013.01)

(58) Field of Classification Search
CPC ................. C07F 15/00; H01L 51/50
USPC ...................... 546/10, 2; 313/504
See application file for complete search history.

(56) References Cited

FOREIGN PATENT DOCUMENTS

| | | |
|---|---|---|
| JP | 2005035902 A | 2/2005 |
| JP | 2008222635 A | 9/2008 |
| JP | 2012077069 A | 4/2012 |
| WO | WO 2015056993 A1 | 4/2015 |

OTHER PUBLICATIONS

K. Noine, et al. Red Phosphorescent Iridium Complexes having a Bulky Ancillary Ligand for Solution-processed Organic Light Emitting Diodes. Journal of Photopolymer Science and Technology, vol. 21(2), 2008, pp. 323-325.

*Primary Examiner* — Charanjit Aulakh
(74) *Attorney, Agent, or Firm* — Orrick, Herrington & Sutcliffe, LLP; Joseph Calvaruso

(57) ABSTRACT

The present invention provides an organic metal complex having high heat resistance while making it possible to realize electroluminescence with high quantum efficiency as a light-emitting material for organic electroluminescent (EL) element. The present invention relates to an organic iridium complex for an organic EL element, wherein a C—N ligand including a substituent of a tricyclic-based structure obtained by condensing a heterocyclic ring and two benzene rings, and a β-diketone ligand composed of a propane-1,3-dione having two tert-butyl-substituted phenyl groups are coordinated with an iridium atom. The complex of the present invention has high heat resistance and contributes to lifetime prolongation of the organic EL element.

20 Claims, 3 Drawing Sheets

1 : Organic EL element
2 : Anode
2a : Glass substrate
3 : Cathode
4 : Light-emitting layer
5 : Hole-injecting layer
6 : Electron-injecting layer

ORGANIC IRIDIUM COMPLEX FOR ORGANIC ELECTROLUMINESCENT ELEMENT

TECHNICAL FIELD

The present invention relates to a technique that provides an organic iridium complex suitable as a light-emitting material for an organic electroluminescent (EL) element, and particularly relates to an organic iridium complex useful as a red a light-emitting material.

BACKGROUND ART

Technical development of the organic EL element is expected as next-generation displays and lighting. The features have advantages of low energy consumption, being capable of making thinner, excellent response speed, being capable of clear image display in both dark and bright places, and the like.

The basic structure of the organic EL element is a sandwich-like structure in which an organic compound of sole layer or multiple layers is sandwiched by a pair of electrodes. Specifically, there is proposed an element having a structure which uses, as a main configuration, a sandwich structure of a cathode/electron transport layer/emission layer/hole transport layer/anode/glass substrate, and which is obtained by appropriately adding a hole (electron)-injecting layer, buffer layer, interlayer insulating film, and the like in order to further enhance the properties. The emission layer which is a center of the sandwich structure uses various light-emitting materials, and the properties of the emission layer are required to easily flow electrons and positive holes which are transported from the cathode and anode, to have excellent light emission efficiency, to be durable, and the like.

Because of those required properties, development of phosphorescent materials has been required instead of the fluorescent materials having been conventionally applied as the light-emitting materials for the organic EL element. Since a generation probability ratio of excited molecule of an excited singlet to that of an excited triplet is 1:3 in the organic EL element, the phosphorescent material which exhibits phosphorescence by transition from the excited triplet state to the ground state is focused on in contrast to the fluorescent material which emits light by transition from the excited singlet to the ground state. Various organic metal complexes have been developed as such phosphorescent materials, and for example, there has been proposed an organic metal complex, as represented by the following Formula, in which a ligand (C—N ligand) having a heterocyclic ring and a C—N structure, and a ligand such as β-diketone are coordinated with a metal atom such as platinum or iridium. Specifically, PTL 1 discloses an organic iridium complex having a ligand with two benzene rings (dibenzoyl methane) as the β-diketone ligand ($SO_2$, etc. in PTL 1). In addition, PTL 2 discloses an organic platinum complex or the like having a ligand with two butoxy-substituted benzene rings (tetra-butoxydiphenyl diketone) as the β-diketone ligand (PTL 2, Formula [1-1]). The light emission efficiency of the organic metal complexes described in the aforementioned PTLs is enhanced by application of the ligands having benzene ring as the β-diketone ligand.

[Chemical Formula 1]

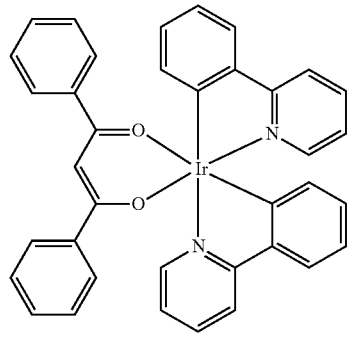

PATENT LITERATURE 1

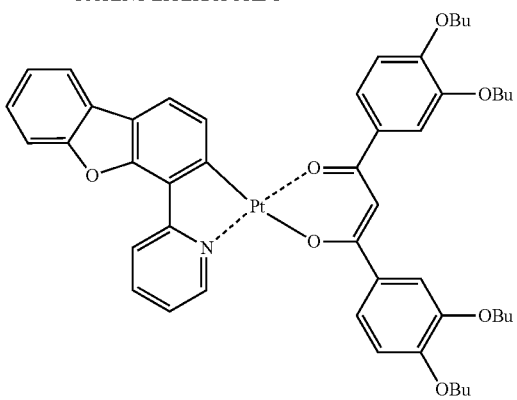

PATENT LITERATURE 2

CITATION LIST

Patent Literature

PTL 1: Japanese Patent Laid-Open Publication No. 2005-35902

PTL 2: Japanese Patent Laid-Open Publication No. 2008-222635

SUMMARY OF INVENTION

Technical Problem

Incidentally, "current efficiency (cd/A)" and "quantum efficiency (%)" are known as a basis for evaluating the light emission efficiency of the organic EL element. The current efficiency exhibits a luminance (or light strength considering visibility) with respect to an amount of current per unit, whereas the quantum efficiency is a percentage of the number of photons capable of being taken out as light energy with respect to an electric power consumption (the number of the injected carriers). In the quantum efficiency, there can be eliminated a part of consumed power which cannot be emitted as light energy (for example, a part of loss due to resistance), of the consumed power. Therefore, when evaluating the light emission efficiency by the quantum efficiency rather than the current efficiency, it is possible to evaluate the light emission efficiency of the organic EL element as a value close to the actual efficiency. Under these circumstances, when considering the organic metal complexes described in PTLs 1 and 2, the complexes do not necessarily have high quantum efficiency although there has been examined the complexes having high current efficiencies as the light emission efficiency. Furthermore, generally, organic metal complexes which particularly exhibit red color tend to have higher quantum efficiency than metal complexes which exhibit blue color or green color. This is due to the essential property of the energy gap law in the molecular optics field. That is because, when the energy gap of the electron transition becomes small, the rate of the non-emitting deactivation of not emitting any light when the state returns from the excited state to the ground state becomes exponentially large. In addition, one of the reasons why the quantum efficiency of the red color is difficult to be high is a structural chemical factor of introducing a complicated C—N ligand (aromatic compound of π-conjugation system, etc) in order to emit light on a long wavelength side.

In addition, the conventional organic metal complexes are required to enhance durability such as heat resistance is required in order to meet the request of lifetime prolongation, in implementation to the organic EL element. In this point, the PTLs 1 and 2 evaluate only the aforementioned current efficiency and the light emission luminance, but do not perform specific examination as to the heat stability.

Accordingly, the present invention is aimed at providing an organic metal complex that has high quantum efficiency and that realizes electroluminescence, as a light-emitting material for the organic EL element, and particularly provides an organic metal complex having high quantum efficiency with respect to a red electroluminescence. Furthermore, the present invention provides an organic metal complex having heat resistance higher than the conventional complexes.

Solution to Problem

For solving the aforementioned problems, the present inventors have focused on an organic iridium complex having iridium as a center atom. Although platinum complexes have also been developed as the organic metal complexes as described in PTL 2, the platinum complex has a high flatness and has an unoccupied ligand in the platinum atom that is the center element, and thus energy loss is easily generated. Specifically, the platinum complex is affected by various interactions including: intermolecular interaction (so-called self-organization) such as association-excimer formation; interaction with a medium such as solvents or matrix (mother materials); furthermore, association with other coexisting molecules; and the like. On the other hand, in the organic iridium complex, since the three ligands have a steric conformation, the aforementioned various interactions as in the platinum complex are not generated, and the energy loss is not easily caused, and thus it is considered that a material having high quantum efficiency is easily obtained.

Moreover, with respect to the quantum efficiency, attention has been focused on a "photoluminescence (PL) quantum yield" of the light-emitting material which is one of the factors that determines the quantum efficiency. When the quantum efficiency is roughly divided into "external photoluminescence quantum efficiency" and "internal photoluminescence quantum efficiency", this PL quantum yield is, as shown in the following equations, one of the factors that determine the internal photoluminescence quantum efficiency. High internal photoluminescence quantum efficiency is required for the light-emitting materials, and particularly, influences of "eficient exciton generation" and "PL quantum yield" are large as the factor that determines the internal photoluminescence quantum efficiency. Among them, since the "eficient exciton generation" is determined depending on the difference in a fluorescent material and a phosphorescent material, the height of the PL quantum yield is important in order to enhance the internal photoluminescence quantum efficiency. Note that carrier balance in the following equation is a factor determined by combination of the materials and element structure such as film thickness control.

[Quantum Efficiency]

External photoluminescence quantum efficiency=
(Efficiency of light extraction)×Internal photoluminescence quantum efficiency Internal photoluminescence quantum efficiency=
(Eficient exciton generation)×(PL quantum yield)×(Carrier balance)

From the above, the present inventors have intensively studied an organic iridium complex for electroluminescent devices having a high PL quantum yield. As a result, the inventors have found an organic iridium complex having tert-butyl substituted-phenyl groups as the β-diketone ligand, and then have conceived the following present invention.

Namely, the present invention relates to an organic iridium complex for an organic electroluminescent (EL) element represented by the following Formula, wherein a C—N ligand including a substituent of a tricyclic-based structure obtained by condensing a heterocyclic ring and two benzene rings, and a β-diketone ligand composed of a propane-1,3-dione having two tert-butyl-substituted phenyl groups are coordinated with an iridium atom.

[Chemical Formula 2]

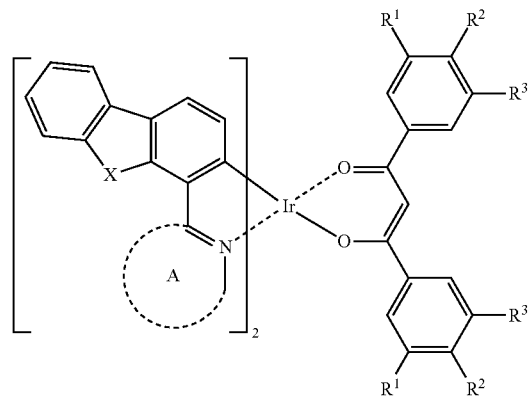

(In the aforementioned Formula, $R^1$, $R^2$, and $R^3$ are each a tert-butyl group or a hydrogen atom, and have at least one tert-butyl group; they may bond each other to thereby form a saturated hydrocarbon ring, when having two tert-butyl groups; A is a substituent having a heterocyclic ring containing nitrogen; X is a hetero atom.)

The present invention has the first feature of employing, as the β-diketone, a bulky substituent of the phenyl group substituted by tert-butyl group, and the present invention adopts the C—N ligand having a specific structure while employing such a β-diketone. Specifically, the present invention employs, as the C—N ligand, the ligand including a tricyclic-based structure obtained by condensing a heterocyclic ring and two benzene rings, and a heterocyclic ring containing nitrogen. In this point, when the structure of an organic metal complex is designed in the conventional techniques, the C—N ligand can be optionally selected from many mentioned structures as long as the desired luminescent color (red, blue, green, etc.) can be emitted, mainly in consideration of the wavelength sift. Namely, enhancement of light emission efficiency has been conventionally achieved by changing the structure of the β-diketone.

In contrast to this, the present inventors have considered that in order to stably obtain an organic iridium complex having high quantum efficiency, it is necessary not only to make the β-diketone ligand have the specific structure, but also to perform the structure design of the C—N ligand in consideration of the compatibility with the β-diketone ligand. However, in the molecular design of the organic iridium complex, it becomes difficult to calculate the PL quantum yield as a numerical value by mechanical calculation or the like because of the complicated interaction between the spins and orbitals derived from Ir. Accordingly, although it is possible to examine respective candidate ligands in consideration of energy level in examining the specific molecular structure, it has been necessary to confirm experimental results by using the complexes having been actually able to synthesized in consideration of possibility of synthesis as complex as to whether each ligand is actually formed into a complex having a high PL quantum yield. From the above results, it has been found that the organic iridium complex: including, as the β-diketone ligand, the propane-1,3-dione with two tert-butyl substituted-phenyl groups as the β-diketone ligand; and including: as the C—N ligand, a skelton including the tricyclic-based structure obtained by condensing a heterocyclic ring and two benzene rings, and the heterocyclic ring containing nitrogen as the C—N ligand would be able to realize high quantum efficiency, and then the present invention has been conceived. Furthermore, the heat resistance of the aforementioned organic iridium complex is higher than that of the conventional complex.

Hereinafter, the organic iridium complex of the present invention will be explained in detail.

The organic iridium complex of the present invention is obtained by coordinating the two C—N ligands and the β-diketone with the trivalent iridium atom. The two C—N ligands have the same structure, and the β-diketone has the line-symmetrical structure. The specific structures of the C—N ligand and the β-diketone ligand will be explained below.

The β-diketone ligand applied to the present invention is composed of the propane-1,3-dione having two tert-butyl-substituted phenyl groups represented by the following Formula.

[Chemical Formula 3]

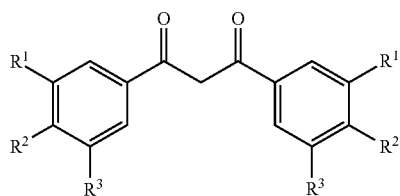

In the above Formula, $R^1$, $R^2$, and $R^3$ are each tert-butyl group or hydrogen atom. One phenyl group has at least one tert-butyl group, preferably two or more tert-butyl groups. The two tert-butyl groups may bond each other to thereby form a saturated hydrocarbon ring.

The structure of the particularly preferable β-diketone ligand is shown below. In the following Formula, t-Bu represents tert-butyl group.

[Chemical Formula 4]

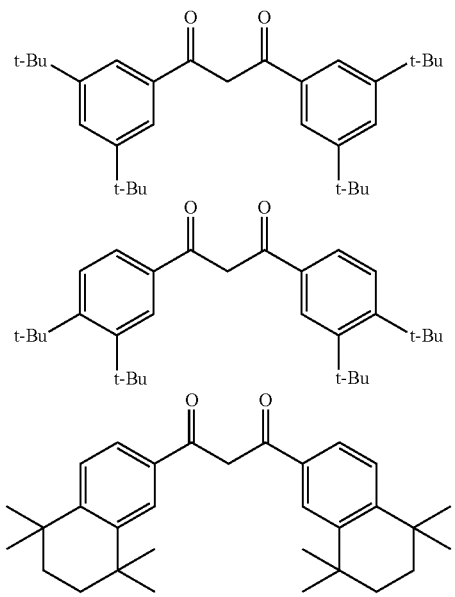

Next, the C—N ligand will be explained. A general formula of the C—N ligand applied to the present invention is represented by the following Formula.

[Chemical Formula 5]

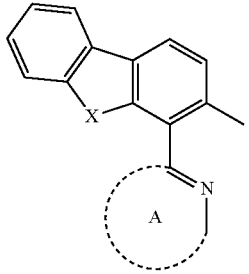

The upper-side substituent in the above C—N ligand has the tricyclic-based structure in which the heterocyclic ring and two benzene rings are condensed. The X in the tricyclic-based structure is a hetero atom. Oxygen atom (O) or sulfur atom (S) may be preferable as the X. In this case, the tricyclic-based structure is dibenzofuran(diphenyleneoxide) or dibenzothiophene(diphenylenesulfide).

The A located on the lower side of the C—N ligand is a substituent having the heterocyclic ring including nitrogen. The heterocyclic ring is preferably a 5-membered ring or a 6-membered ring. Furthermore, the A may preferably have a structure obtained by condensing the heterocyclic ring including nitrogen and the benzene ring. The heterocyclic ring or the benzene ring of the A may have an optional substituent at a side chain, and the substituent may be either an electron donating group or an electron withdrawing group. Examples of the substituent include an alkyl group (—R, 1 to 5 carbons), an alkoxy group (—OR, 1 to 3 carbons), a halogen atom (particularly fluorine atom), a halogenated alkyl group (1 to 5 carbons), and the like. The heterocyclic ring of the A may further include a heteroatom other than nitrogen (N), and an example of the preferred heteroatom other than nitrogen (N) is sulfur atom (S) or oxygen atom (O).

The particularly preferable substituent A may be any of the substituents shown in the following substituents represented by the following Formula.

[Chemical Formula 6]

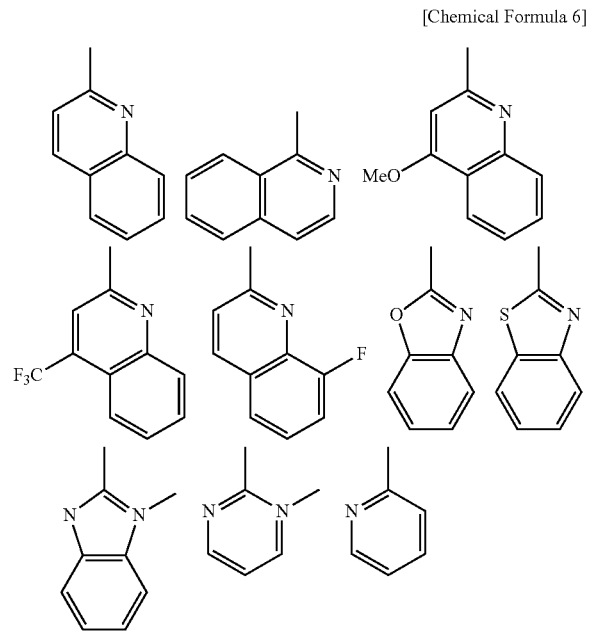

As explained above, the organic iridium complex of the present invention has high light emission efficiency, and when 4 wt % doping is performed in a polymer thin film, the PL quantum yield $\phi_{PL}$ tends to be high (for example, 0.4 or more). In addition, the organic iridium complex of the present invention has a high decomposition temperature and is excellent in thermal stability. Therefore, the organic iridium complex of the present invention is suitable for implementation to the organic EL element as the emission layer.

The organic iridium complex can be synthesized by reacting an iridium salt and a nitrogen-containing compound that constitutes the C—N ligand with each other by heating to thereby give a precursor, and then by reacting the precursor and a β-diketone compound with each other by heating. Alternatively, the organic iridium complex can also be synthesized by reacting a metal salt with a β-diketone compound, and then by reacting the resultant compound with a nitrogen-containing compound. The heating reaction for obtaining the precursor is preferably carried out at 80° C. to 130° C. for 12 to 24 hours, and the heating reaction with the β-diketone is preferably carried out at 60° C. to 130° C. for 0.5 to 12 hours. The reactions are preferably carried out in the presence of a solvent. The preferred iridium salt to be used in the aforementioned synthetic reaction is an Iridium Chloride (IrCl3). Furthermore, a hydrate of the chloride can be used as the form of use.

When the organic iridium complex mentioned above is applied to the organic EL element, the emission layer can be formed by a method such as spin coating method or vacuum deposition method. An element can be easily and inexpensively formed in the spin coating method.

Advantageous Effects of Invention

The organic iridium complex of the present invention is suitable as a light-emitting material of the organic EL element because of higher PL quantum yield and heat resistance than those of the conventional complexes.

DESCRIPTION OF EMBODIMENTS

Figure 1:
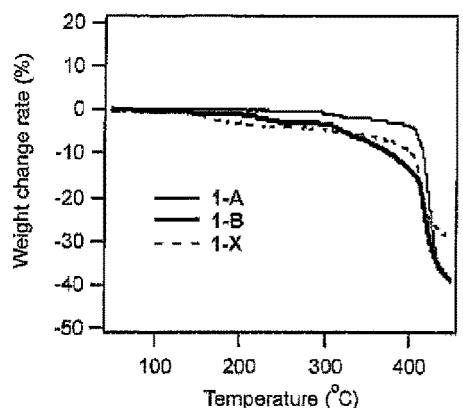
FIG. 1 shows the results of the thermal decomposition property of the organic iridium complex according to the embodiment.
Figure 1:
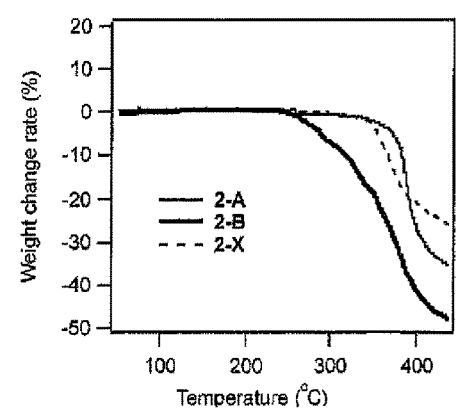
Figure 1:
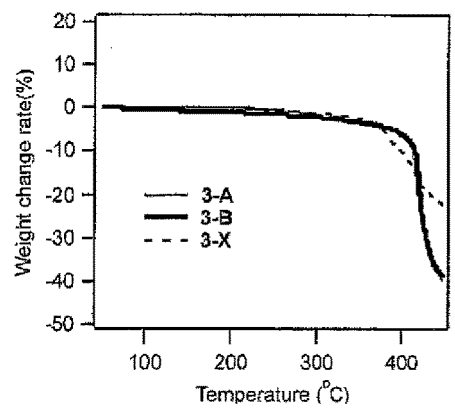
Figure 1:
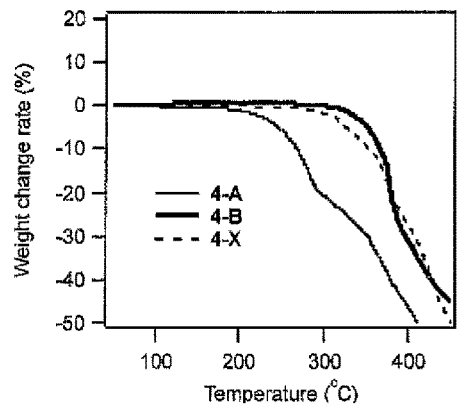

Hereinafter, there will be explained the preferred embodiments according to the present invention.

The following organic iridium complexes were synthesized, and the quantum efficiency and the thermal decomposition property of the obtained complexes were evaluated.

[Chemical Formula 7]

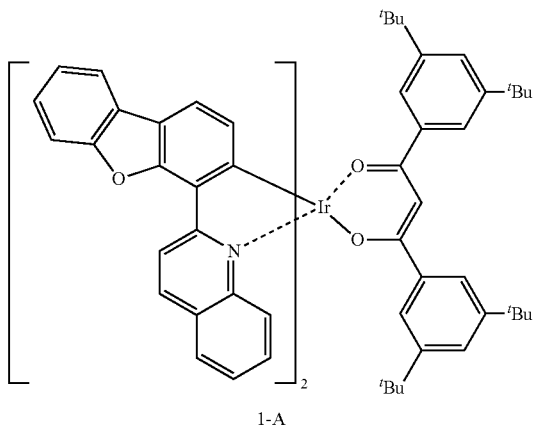

1-A

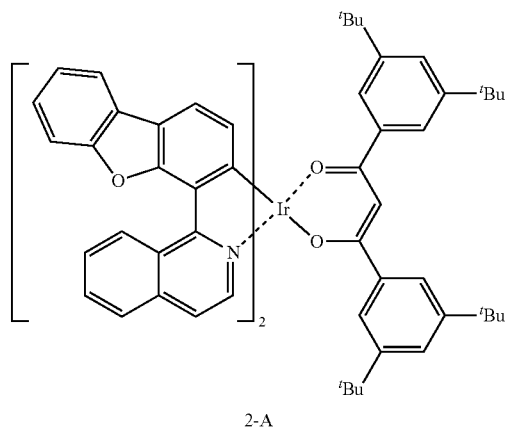

2-A

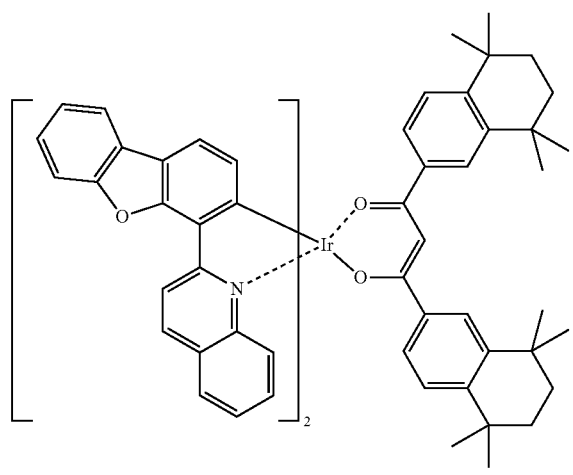
1-B
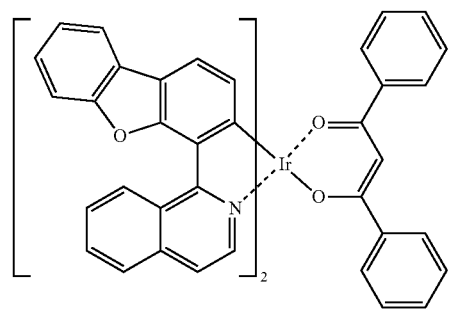
2-X
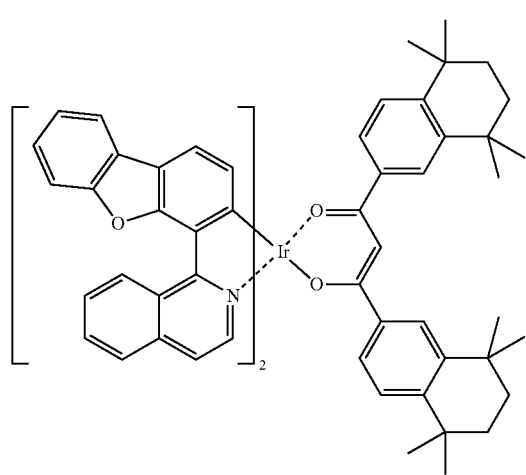
2-B
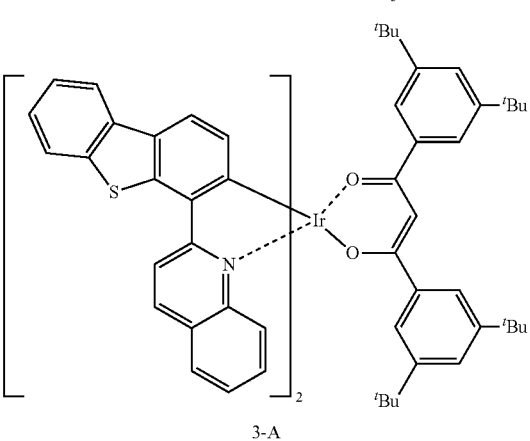
3-A
[Chemical Formula 8]
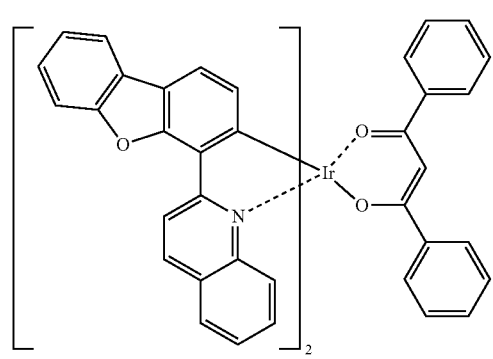
1-X
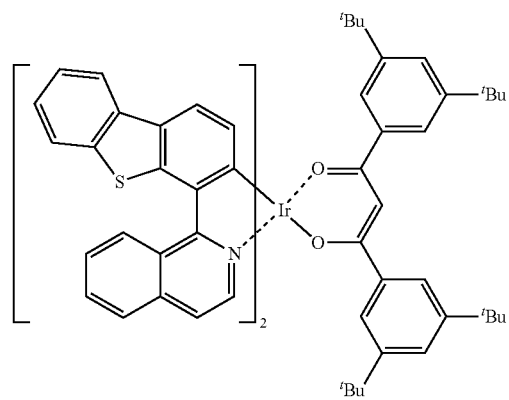
4-A -continued

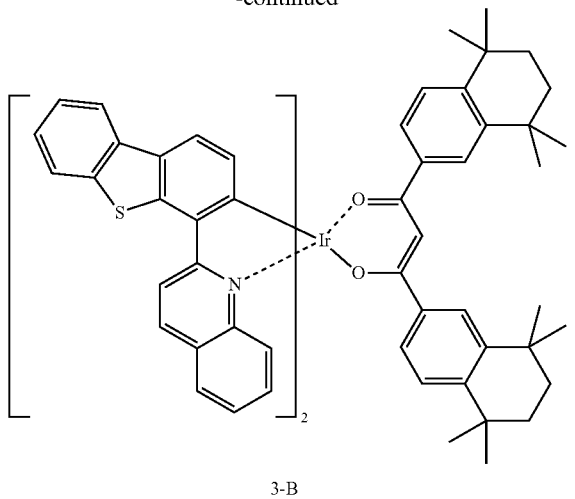

3-B

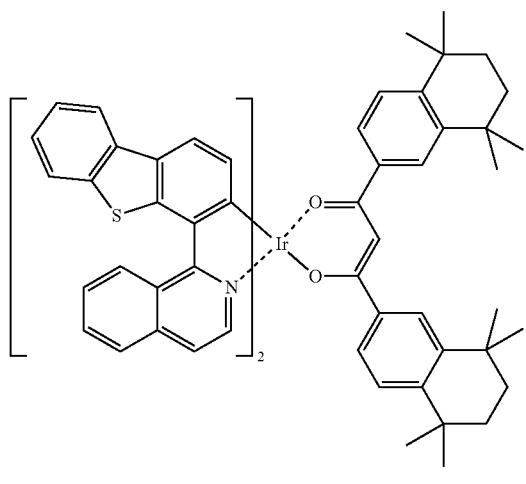

4-B

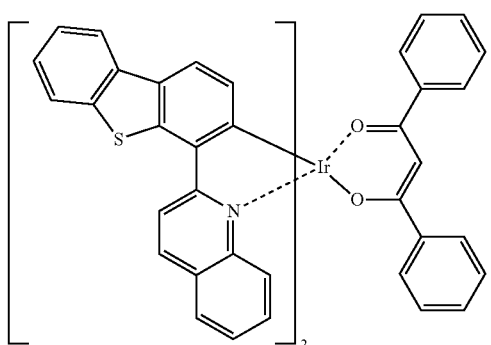

3-X

-continued

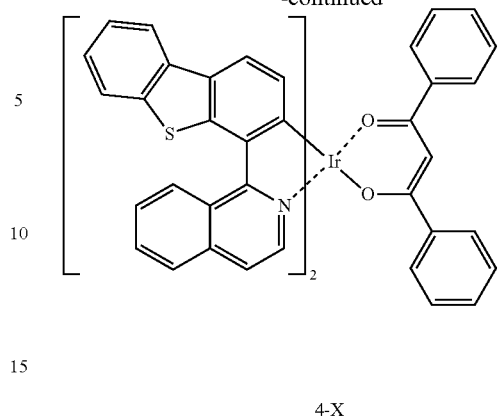

4-X

An outline of the synthetic procedures of each iridium complex will be explained by taking, as an example, the synthetic procedures of the complex 1-A. A β-diketone compound (A) and a C—N ligand(1:2-(dibenzo[b,d]furan-4-yl)quinoline) were synthesized, and a precursor (1) was synthesized by reacting the ligand (1) with iridium chloride. Then, the iridium complex 1-A was obtained by reacting the precursor (1) with the β-diketone compound. The other complexes were obtained in the same way by synthesizing a β-diketone compound (B), ligands (2) to (4), and precursors (2) to (4), and then reacting each precursor with each β-diketone compound.

All of the starting materials, the reagents and solvents used for the synthesis were those having commercially available reagent grades without purification. The commercially available dehydrated THF was used as the dry THF as it was. In addition, a spherical silica gel (neutral) manufactured by KANTO CHEMICAL CO., INC. was used as a filler to be used for a column chromatography.

A proton nuclear magnetic resonance ($^1$H NMR) spectrum and a mass analysis (mass (MS) spectrum) were used for identification of the synthesized compounds. Jeol JNM-ECX400 spectrophotometer (400 MHz) or Jeol JNM-ECS400 spectrophotometer (400 MHz) were used for measurement of the $^1$H NMR spectrum. The MS spectrum was measured by subjecting a sample ionized by a matrix-assisted laser desorption ionization method (MALDI method) to the time-of-flight (TOF) type mass spectrometry by using α-cyano-4-hydroxycinnamic acid (CHCA) as a matrix (MALDI-TOF-MS spectrum). Used for the measurement was Shimadzu-Kratos AXIMA-CFR PLUS TOF Mass mass spectrometry analyzer. Elemental analysis was performed by JM-10 elemental analysis machine manufactured by J-Science Lab CO. Ltd. by using acetanilide as a standard substance.

First, the synthetic procedures of the β-diketone compounds (A) and (B) will be explained.

SYNTHESIS OF β-DIKETONE COMPOUND (A)

After methyl dibutylbenzoate and (methyl dibutylbenzoate)ethane-1-on were synthesized, the β-diketone compound (A) was obtained by the synthetic reaction using these two compounds.

<Synthesis of methyl 3,5-di-tert-butylbenzoate>

A concentrated sulfuric acid (0.9 mL) was dropped onto a mixture of 3,5-di-tert-butylbenzoic acid (3.00 g, 12.8 mmol) and methanol (9 mL) under a nitrogen atmosphere at 0° C., followed by heating and refluxing the resulting substance for 1 hour with stirring. After being allowed to cool, chloroform (100 mL) was added, and further water (100 mL) was added, with the result that an organic layer was separated by shaking in a separating funnel. After repeating this procedure again, the separated organic layers were combined into one. After further washing the organic layer with a saturated aqueous sodium bicarbonate solution (50 mL) and a saturated saline (50 mL), the organic layer was then dried by addition of an appropriate amount of anhydrous magnesium sulfate. After removal of the magnesium sulfate by filtration, methyl 3,5-di-tert-butylbenzoate was obtained by distilling the solvent with an evaporator, and by drying the residue in a desiccator under a reduced pressure. The obtained compound was a white solid, and a yield was 92% (2.92 g, 11.8 mmol). The properties ($^1$H NMR, TOF MS) of the compound thus synthesized were as follows.

<Synthesis of methyl 3,5-di-tert-butylbenzoate>

A concentrated sulfuric acid (0.9 mL) was dropped onto a mixture of 3,5-di-tert-butylbenzoic acid (3.00 g, 12.8 mmol) and methanol (9 mL) under a nitrogen atmosphere at 0° C., followed by heating and refluxing the resulting substance for 1 hour with stirring. After being allowed to cool, chloroform (100 mL) was added, and further water (100 mL) was added, with the result that an organic layer was separated by shaking in a separating funnel. After repeating this procedure again, the separated organic layers were combined into one. After further washing the organic layer with a saturated aqueous sodium bicarbonate solution (50 mL) and a saturated saline (50 mL), the organic layer was dried by addition of an appropriate amount of anhydrous magnesium sulfate. After removal of the magnesium sulfate by filtration, methyl 3,5-di-tert-butylbenzoate was obtained by distilling the solvent with an evaporator, and by drying the residue in a desiccator under a reduced pressure. The obtained compound was a white solid, and a yield was 92% (2.92 g, 11.8 mmol). The properties ($^1$H NMR, TOF MS) of the compound thus synthesized were as follows.

$^1$H NMR (CDCl$_3$): δ1.35 (s, 18H), 3.91 (s, 3H), 7.62 (t, J=2.0 Hz, 1H), 7.89 (d, J=2.0 Hz, 2H)

MALDI-TOF MS: m/z 249 ([M+H]$^+$)

[Chemical Formula 9]

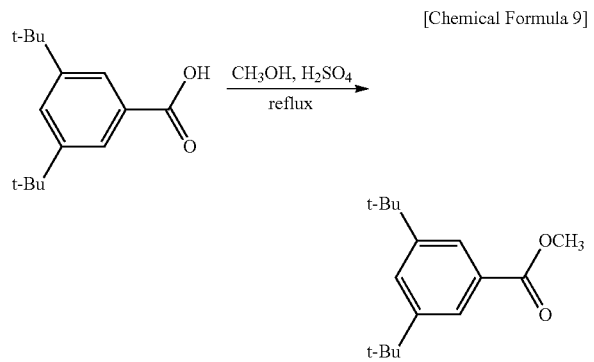

<Synthesis of 1-(methyl 3,5-di-tert-butylbenzoate)ethane-1-on>

3,5-di-tert-t-butylbenzoic acid (3.00 g, 12.8 mmol) was added to a dry tetrahydrofuran (120 mL), and was cooled to 0° C. or less with stirring under a nitrogen atmosphere. 3.0 M methyl lithium solution in diethoxymethane (15 mL) was dropped onto the mixture, and after raising the temperature to a room temperature, was stirred for 2 hours. After adding a 6 M hydrochloric acid to the reaction mixture to be acidic, extraction with chloroform (100 mL×2) was carried out. The obtained organic layers were combined into one, and after washing with water (50 mL×2), a saturated aqueous sodium bicarbonate solution (50 mL) and a saturated saline (50 mL), an appropriate amount of anhydrous magnesium sulfate was added for drying. After removal of the magnesium sulfate by filtration, 1-(3,5-di-tert-butylphenyl)ethane-1-on was obtained by distilling the solvent with an evaporator, and by purifying the residue with a silica gel column chromatography (development solvent; chloroform). The obtained compound was a colorless liquid, and a yield was 75% (2.23 g, 9.60 mmol). The properties of the thus obtained compound were as follows.

$^1$H NMR (CDCl$_3$) δ1.37 (s, 18H), 2.60 (s, 3H), 7.64 (t, J=1.6 Hz, 1H), 7.80 (d, J=1.6 Hz, 2H)

MALDI-TOF MS: m/z 232 (M$^+$)

[Chemical Formula 10]

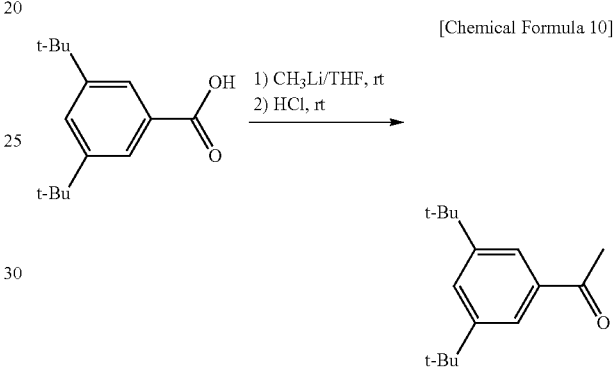

<Synthesis of β-diketone Compound (A)>

Methyl 3,5-di-tert-butylbezoate (2.92 g, 11.8 mmol) and sodium hydride (60% oil dispersion; 1.27 g, 31.8 mmol) were added to a dry THF (23 mL), and were stirred at a room temperature under a nitrogen atmosphere. Then, a solution obtained by dissolving the 1-(3,5-di-tert-butylphenyl)ethane-1-on (2.23 g, 9.60 mmol) in a dry THF (23 mL) was dropped onto the resultant substance for 30 minutes. Subsequently, the obtained reaction mixture was stirred for 24 hours at 60° C. After being allowed to cool, and after adding a 1 M hydrochloric acid to be acidic, extraction with chloroform (100 mL×2) was carried out. The obtained organic layers were combined into one, and after washing with water (50 mL×2), a saturated aqueous sodium bicarbonate solution (50 mL) and a saturated saline (50 mL), an appropriate amount of anhydrous magnesium sulfate was added for drying. After removal of the magnesium sulfate by filtration, 1,3-bis(3,5-di-tert-butylphenyl) propane-1,3-dion (β-diketone A) was obtained by distilling the solvent with an evaporator, and by purifying the residue with a silica gel column chromatography (development solvent; chloroform). The obtained compound was an amber syrup substance, and a yield was 49% (2.12 g, 4.73 mmol). The properties of the thus obtained compound were as follows.

$^1$H NMR (CDCl$_3$) δ1.38 (s, 36H), 6.78 (s, 1H), 7.63 (t, J=2.0 Hz, 2H), 7.78 (d, J=2.0 Hz, 4H), 16.9 (brs, 1H)

MALDI-TOF MS: m/z 449 ([M+H]$^+$)

[Chemical Formula 11]

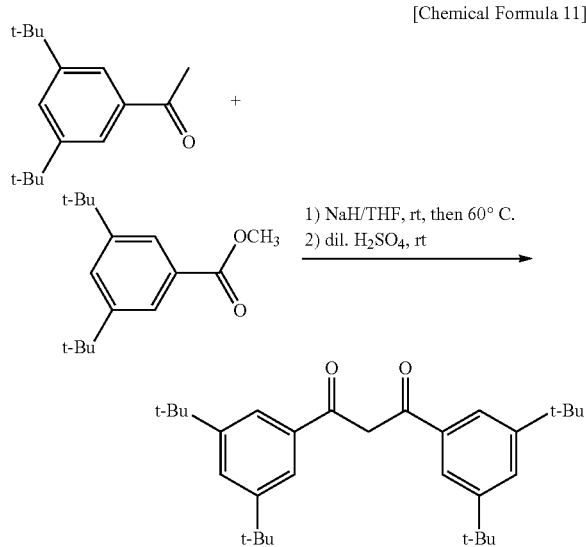

SYNTHESIS OF β-DIKETONE COMPOUND (B)

The β-diketone compound (B) was obtained by the synthetic reaction of 1,2,3,4-tetrahydro-1,1,4,4-tetramethyl-naphthalene and malonyl chloride.

<Synthesis of β-diketone Compound (B)>

1,2,3,4-tetrahydro-1,1,4,4-tetramethylnaphthalene (5.00 g, 26.6 mmol), malonyl chloride (1.35 g, 9.58 mmol) and aluminum chloride (5.51 g, 41.3 mmol) were added to carbon disulfide (27 mL), and were heated and stirred at 50° C. for 3 hours. Next, after being allowed to cool, a cold 2 mol/L hydrochloric acid (27 mL) was added, and after transferring to a separatory funnel, extraction was carried out with chloroform. The organic layer was further washed with water, and after distilling the solvent with an evaporator, a concentrated hydrochloric acid (3.5 mL) and chloroform (35 mL) were added, and were then heated and refluxed for 9 hours. After being allowed to cool, the mixture was transferred to a separatory funnel, and was washed with water and a saturated saline. The solvent was distilled off with a rotary evaporator after drying the organic layer by using an anhydrous magnesium sulfate. The β-diketone (B) was obtained in a yield of 39% (1.66 g, 3.74 mmol) by purifying the residue with a silica gel column chromatography (development solvent; ethyl acetate: hexane=1:2 (v/v)). The properties of the thus obtained compound were as follows.

$^1$H NMR (CDCl$_3$): δ1.30 (s, 12H), 1.34 (s, 12H), 1.71 (m, 8H), 6.76 (s, 1H), 7.40 (d, J=8.0 Hz, 2H), 7.68 (dd, J=8.0 and 2.0 Hz, 2H), 7.94 (d, J=2.0 Hz, 2H), 16.96 (brs, 1H)

MALDI-TOF MS: m/z 445 ([M+H]$^+$)

[Chemical Formula 12]

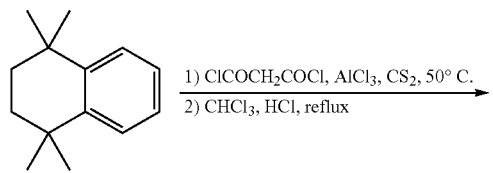

-continued

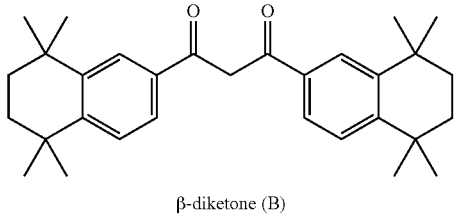

β-diketone (B)

Next, the synthetic procedures of the C—N ligands (1) to (4), and the precursors (1) to (4) will be explained.

Synthesis of C—N Ligand (1)

According to the following Formula, 2-(dibenzo[b,d]furan-4-yl)quinoline was synthesized as the C—N ligand (1).

[Chemical Formula 13]

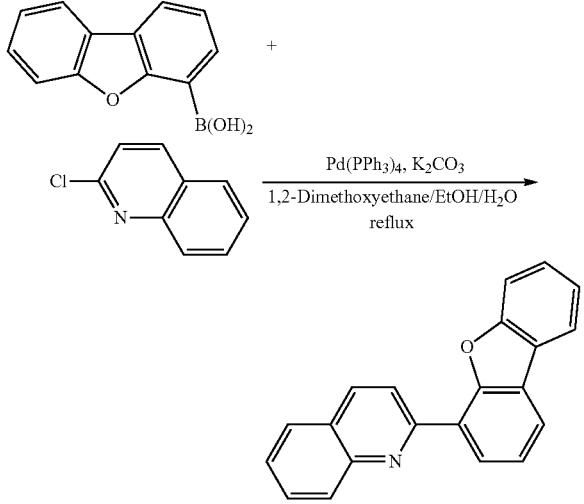

A mixture of dibenzo[b,d]furan-4-yl borate (1.44 g, 6.79 mmol), 2-chloroquinoline (1.24 g, 7.58 mmol), tetrakis(triphenylphosphine)palladium (0.658 g, 0.569 mmol) and potassium carbonate (14.4 g, 104 mmol) was added to a mixed solvent of 1,2-dimethoxyethane (75 mL), ethanol (75 mL) and water (75 mL), and the resultant mixture was heated and refluxed for 18 hours on a hot water bath set at 100° C. under a nitrogen atmosphere. After the resultant substance was allowed to cool, the organic solvent was distilled off with an evaporator, and then 100 mL of chloroform was added. The resultant mixture was washed with water (2×100 mL) and a saturated saline (100 mL), and was then dried by adding an appropriate amount of magnesium sulfate. After removal of the magnesium sulfate by filtration, the solvent of the filtrate was distilled off with an evaporator. 2-(dibenzo[b, d]furan-4-yl)quinoline was obtained in a yield of 79% (1.59 g, 5.38 mmol) by purifying the obtained residue with a silica gel column chromatography development solvent; chloroform). The properties of the thus obtained compound were as follows.

$^1$H NMR (CDCl$_3$): δ7.39 (t, J=7.6 Hz, 1H), 7.48-7.53 (m, 1H), 7.55-7.59 (m, 2H), 7.66 (d, J=8.7 Hz, 1H), 7.76 (dt, J=1.4 and 7.6 Hz, 1H), 7.89 (d, J=7.6 Hz, 1H), 8.02 (d, J=7.6 Hz, 1H), 8.06 (dd, J=1.4 and 7.6 Hz, 1H), 8.23 (d, J=8.7 Hz, 1H), 8.34 (d, J=8.7 Hz, 1H), 8.43 (dd, J=1.4 and 7.6 Hz, 1H), 8.52 (d, J=8.7 Hz, 1H)

MALDI-TOF MS: m/z 296 ([M+H]$^+$)

Synthesis of Precursor (1)

According to the following Formula, a precursor (1) was obtained by casing the C—N ligand (1) and iridium chloride to react with each other. A mixture of 2-(dibenzo[b,d]furan-4-yl)quinoline (3.50 g, 11.9 mmol) and 2-ethoxyethanol (210 mL) was heated on an oil bath under a nitrogen atmosphere. When the temperature of the solution reached 100° C., a mixture of iridium chloride trihydrate (1.60 g, 4.54 mmol) and water (70 mL) was added, and the thus obtained reaction mixture was stirred for 10 hours at 120° C. After being allowed to cool, water (175 mL) was added to the reaction mixture, the resulting precipitant was recovered by filtration, and then the precursor (1) was obtained in a yield of 83% (3.08 g, 1.89 mmol) by washing with an appropriate amount of methanol. The thus obtained compound was an insoluble solid. Without further purification, the compound was used for the following synthesis of an iridium complex.

[Chemical Formula 14]

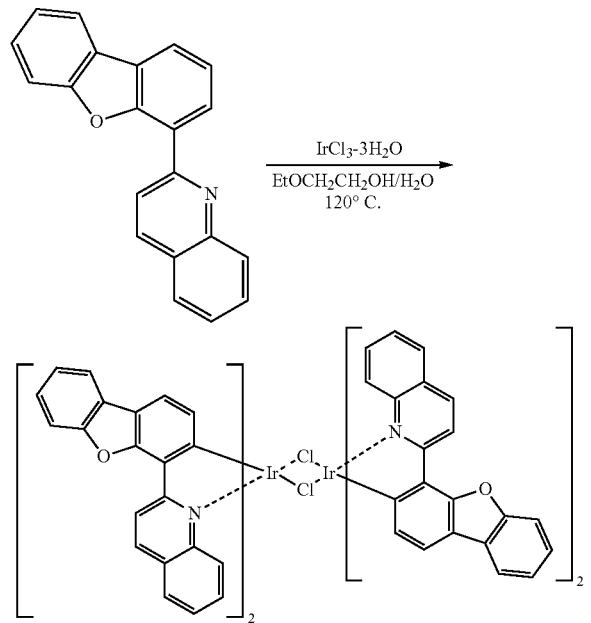

Synthesis of C—N Ligand (2)

According to the following Formula, 1-(dibenzo[b,d]furan-4-yl)isoquinoline was synthesized as the C—N ligand (2).

[Chemical Formula 15]

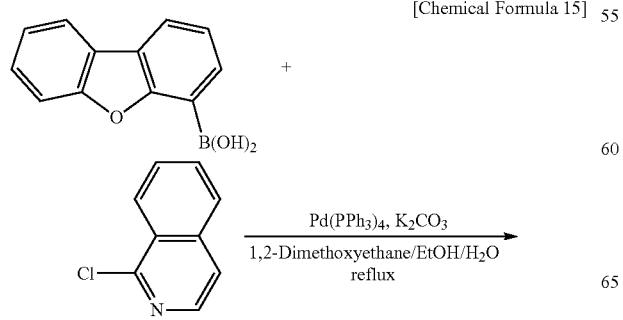

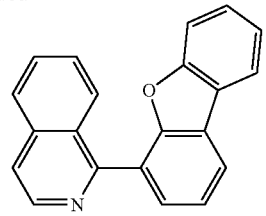

A mixture of dibenzo[b,d]furan-4-yl borate (5.00 g, 23.6 mmol), 1-chloroisoquinoline (4.19 g, 25.6 mmol), tetrakis(triphenylphosphine)palladium (0) (2.27 g, 1.96 mmol) and potassium carbonate (49.2 g, 356 mmol) was added to a mixed solvent of 1,2-dimethoxyethane (150 mL), ethanol (150 mL) and water (150 mL), and the resultant mixture was heated and refluxed for 12 hours under a nitrogen atmosphere. After being allowed to cool, water and ethyl acetate were added to the reaction mixture and the resultant compound was shaken in a separatory funnel, and the layer was washed with a saturated saline after separating the organic layer, and was then dried by adding an appropriate amount of magnesium sulfate. After removal of the magnesium sulfate by filtration, the solvent of the filtrate was distilled off with an evaporator. 1-(dibenzo[b,d]furan-4-yl)isoquinoline was obtained in a yield of 74% (5.18 g, 17.5 mmol) by purifying the obtained residue with a silica gel column chromatography (development solvent; chloroform:hexane=1:3 (v/v)). The properties of the thus obtained compound were as follows.

$^1$H NMR (CDCl$_3$): δ7.36-7.40 (m, 1H), 7.41-7.42 (m, 2H), 7.46-7.55 (m, 2H), 7.67-7.74 (m, 2H), 7.77 (d, J=6.0 Hz, 1H), 7.83 (d, J=8.8 Hz, 1H), 7.94 (d, J=8.4 Hz, 1H), 8.00-8.04 (m, 1H), 8.11 (dd, J=1.4 Hz and 5.6 Hz, 1H), 8.72 (d, J=5.6 Hz, 1H)

MALDI-TOF MS: m/z 296 ([M+H]$^+$)

Synthesis of Precursor (2)

According to the following Formula, a precursor (2) was obtained by reacting the C—N ligand (2) with iridium chloride. A mixture of 1-(dibenzo[b,d]furan-4-yl)isoquinoline (3.07 g, 10.4 mmol) and 2-ethoxyethanol (180 mL) was heated on an oil bath under a nitrogen atmosphere. When the temperature of the solution reached 100° C., a mixture of iridium chloride trihydrate (1.21 g, 4.04 mmol) and water (60 mL) was added, and the thus obtained reaction mixture was stirred for 10 hours at 120° C. After being allowed to cool, water (150 mL) was added to the reaction mixture, the resulting precipitant was recovered by filtration, and then the precursor (2) was obtained in a yield of 69% (2.28 g, 1.40 mmol) by washing with an appropriate amount of methanol. Since the thus obtained precursor (2) was an insoluble solid, the compound was used for the following synthesis of an iridium complex without further purification.

[Chemical Formula 16]

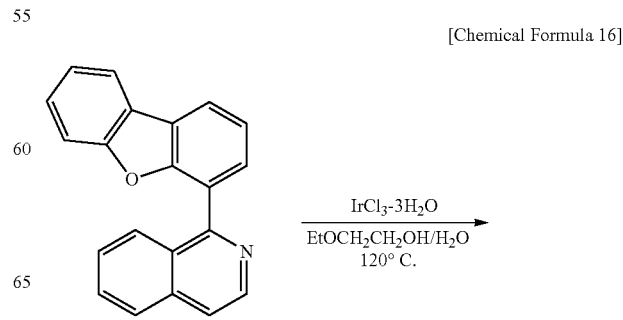

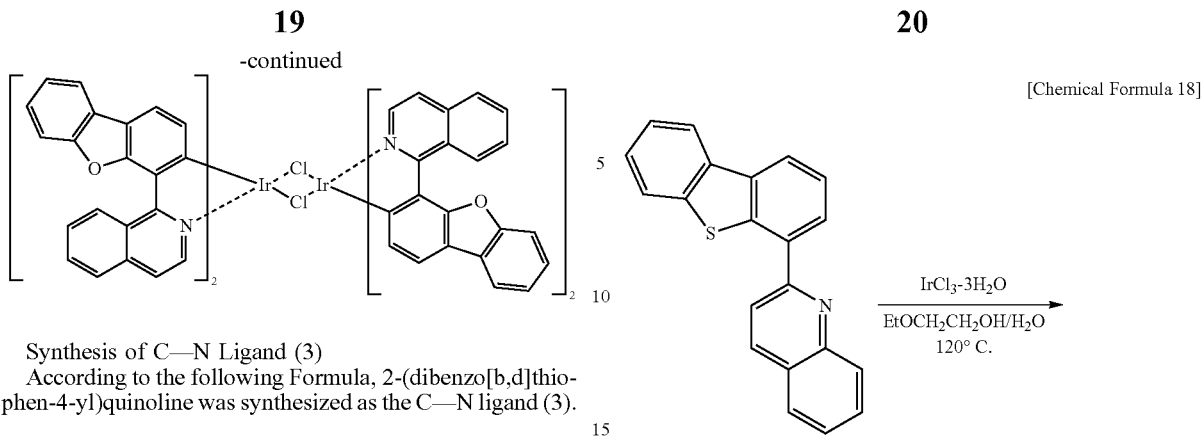

Synthesis of C—N Ligand (3)

According to the following Formula, 2-(dibenzo[b,d]thiophen-4-yl)quinoline was synthesized as the C—N ligand (3).

[Chemical Formula 17]

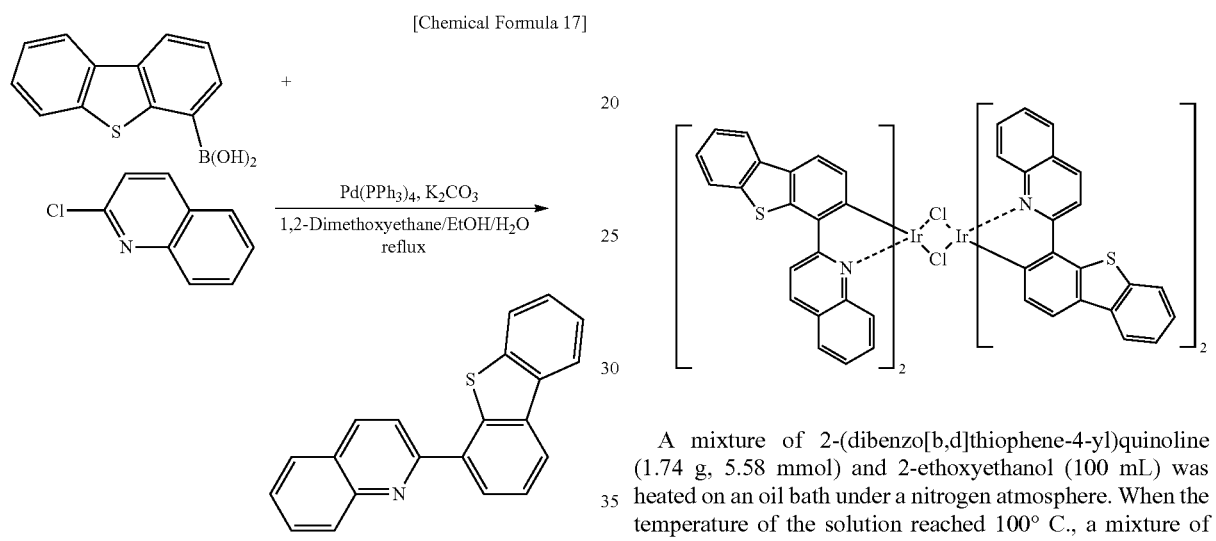

A mixture of dibenzo[b,d]thiophene-4-yl borate (1.60 g, 7.01 mmol), 2-chloroquinoline (1.27 g, 7.76 mmol), tetrakis (triphenylphosphine)palladium (0.665 g, 0.575 mmol) and potassium carbonate (14.8 g, 107 mmol) was added to a mixed solvent of 1,2-dimethoxyethane (75 mL), ethanol (75 mL) and water (75 mL), and the resultant mixture was was heated and refluxed for 18 hours on an oil bath set at 100° C. under a nitrogen atmosphere. After being allowed to cool, the organic solvent was distilled off with an evaporator, and then 100 mL of chloroform was added. The mixture was washed with water and a saturated saline, and was then dried by adding an appropriate amount of magnesium sulfate. After removal of the magnesium sulfate by filtration, the solvent of the filtrate was distilled off with an evaporator. 2-(dibenzo[b,d]thiophene-4-yl)quinoline was obtained in a yield of 89% (1.94 g, 6.23 mmol) by purifying the obtained residue with a silica gel column chromatography (development solvent; chloroform:hexane=2.5:1 (v/v)). The properties of the thus obtained compound were as follows.

$^1$H NMR (CDCl$_3$): δ7.46-7.53 (m, 2H), 7.58 (dt, J=1.4 and 7.6 Hz, 1H), 7.63 (t, J=7.8 Hz, 1H), 7.80 (dt, J=1.4 and 7.6 Hz, 1H), 7.86 (d, J=7.8 Hz, 1H), 7.99 (m, 1H), 8.10 (d, J=8.7 Hz, 1H), 8.17 (dd, J=1.4 and 7.6 Hz, 1H), 8.21-8.24 (m, 1H), 8.26 (d, J=8.7 Hz, 1H), 8.30 (dd, J=0.9 and 7.8 Hz, 1H), 8.42 (d, J=7.8 Hz, 1H)

MALDI-TOF MS: m/z 311 (M$^+$)

Synthesis of Precursor (3)

According to the following Formula, a precursor (3) was synthesized by reacting the C—N ligand (3) and iridium chloride with each other.

[Chemical Formula 18]

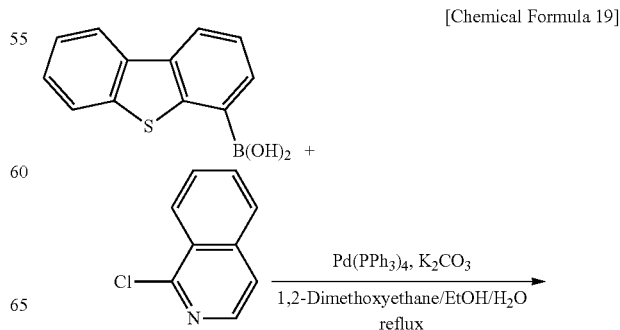

A mixture of 2-(dibenzo[b,d]thiophene-4-yl)quinoline (1.74 g, 5.58 mmol) and 2-ethoxyethanol (100 mL) was heated on an oil bath under a nitrogen atmosphere. When the temperature of the solution reached 100° C., a mixture of iridium chloride trihydrate (1.24 g, 3.52 mmol) and water (35 mL) was added, and the thus obtained reaction mixture was stirred for 10 hours at 120° C. After being allowed to cool, water (90 mL) was added to the reaction mixture, the resulting precipitant was recovered by filtration, and then the precursor (3) was obtained in a yield of 89% (2.11 g, 1.24 mmol) by washing with an appropriate amount of methanol. The thus obtained compound was an insoluble solid. The compound was used for the following synthesis of an iridium complex without further purification.

Synthesis of C—N Ligand (4)

According to the following Formula, 1-(dibenzo[b,d]thiophen-4-yl)isoquinoline was synthesized as the C—N ligand (4).

[Chemical Formula 19]

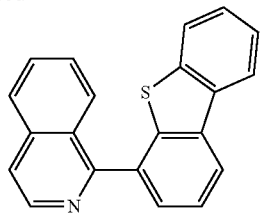

A mixture of dibenzo[b,d]thiophene-4-yl borate (1.57 g, 6.88 mmol), 1-chloroisoquinoline (1.24 g, 7.58 mmol), tetrakis(triphenylphosphine)palladium (0.688 g, 0.595 mmol) and potassium carbonate (14.7 g, 106 mmol) was added to a mixed solvent of 1,2-dimethoxyethane (75 mL), ethanol (75 mL) and water (75 mL), and the resultant mixture was heated and refluxed for 18 hours on an oil bath set at 100° C. under a nitrogen atmosphere. After being allowed to cool, the organic solvent was distilled off with an evaporator, and then 100 mL of chloroform was added. The mixture was washed with water and a saturated saline, and was then dried by adding an appropriate amount of magnesium sulfate. After removal of the magnesium sulfate by filtration, the solvent of the filtrate was distilled off with an evaporator. 1-(dibenzo[b,d]thiophene-4-yl)isoquinoline was obtained in a yield of 77% (1.65 g, 5.30 mmol) by purifying the obtained residue with a silica gel column chromatography (development solvent; chloroform:hexane=2:1 (v/v)). The properties of the thus obtained compound were as follows.

$^1$H NMR (CDCl$_3$): δ7.44-7.53 (m, 3H), 7.64 (t, J=7.8 Hz, 1H), 7.69-7.72 (m, 2H), 7.74-7.79 (m, 2H), 7.94 (d, J=8.3 Hz, 1H), 7.98 (d, J=7.8 Hz, 1H), 8.21-8.24 (m, 1H), 8.29 (dd, J=7.6 Hz, 1H), 8.71 (d, J=6.0 Hz, 1H)

MALDI-TOF MS: m/z 311 (M$^+$)

Synthesis of Precursor (4)

According to the following Formula, a precursor (4) was synthesized by reacting the C—N ligand (4) and iridium chloride with each other.

[Chemical Formula 20]

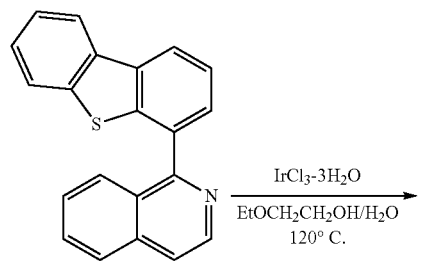

A mixture of 1-(dibenzo[b,d]thiophene-4-yl)isoquinoline (1.65 g, 5.30 mmol) and 2-ethoxyethanol (100 mL) was heated on an oil bath under a nitrogen atmosphere. When the temperature of the solution reached 100° C., a mixture of iridium chloride trihydrate (1.06 g, 3.01 mmol) and water (35 mL) was added, and the thus obtained reaction mixture was stirred for 10 hours at 120° C. After being allowed to cool, water (90 mL) was added to the reaction mixture, the resulting precipitant was recovered by filtration, and then the precursor (4) was obtained in a yield of 71% (1.60 g, 0.943 mmol) by washing with an appropriate amount of methanol. The thus obtained compound was an insoluble solid. The compound was used for the following synthesis of an iridium complex without further purification.

The thus synthesized precursors (1) to (4) and the β-diketone compounds (A) and (B) were reacted with each other in the following way to give each iridium complex (1-A, 1-B, 1-X, 2-A, 2-B, 2-X, 3-A, 3-B, 3-X, 4-A, 4-B, and 4-X).

Synthesis of Iridium Complex (1-A)

According to the following Formula, the iridium complex 1-A was obtained by reacting the precursor (1) and the β-diketone (A) with each other.

[Chemical Formula 21]

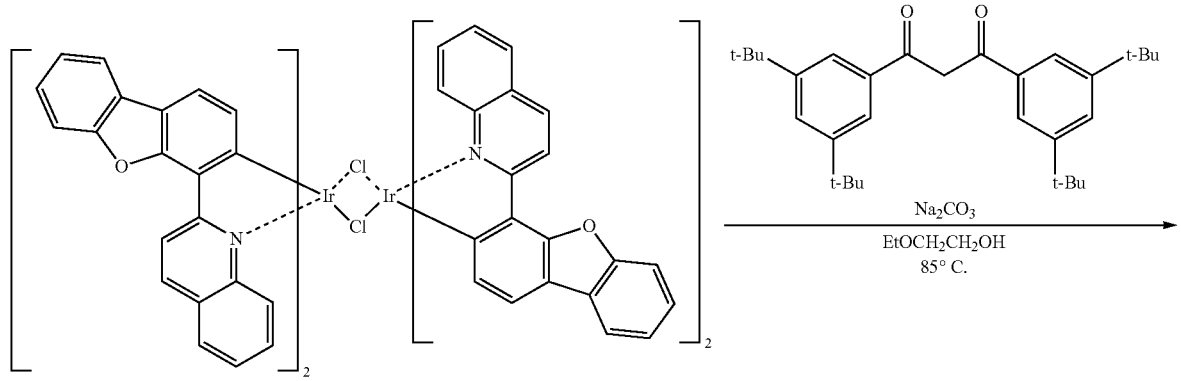

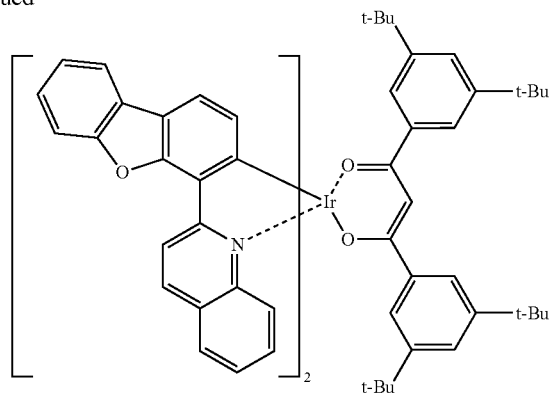

The precursor (1) (0.482 g, 0.295 mmol), 1,3-bis(3,5-di-tert-butyl phenyl)propane-1,3-dione (0.223 g, 0.497 mmol) and sodium carbonate (0.382 g, 3.60 mmol) was added to 2-ethoxyethanol (100 mL), and the resulting mixture was stirred for 2 hours at 85° C. under a nitrogen atmosphere. After being allowed to cool, the solvent was distilled off under a reduced pressure, and then chloroform was added to the residue. The obtained mixed solution was washed with water and a saturated saline, and was then dried by adding an appropriate amount of sodium sulfate. After removal of the sodium sulfate by filtration, the solvent of the filtrate was distilled off with an evaporator. The iridium complex 1-A was obtained in a yield of 17% (106 mg, 0.0862 mmol) by purifying the obtained residue with an alumina column chromatography (development solvent; chloroform:hexane=1:3 (v/v)), and by further performing recrystallization using chloroform-methanol. The properties of the thus synthesized compound were as follows.

$^1$H NMR (CDCl$_3$): δ1.17 (s, 36H), 5.75 (s, 1H), 6.67 (d, J=8.2 Hz, 2H), 7.06 (d, J=1.8 Hz, 4H), 7.19-7.23 (m, 4H), 7.28 (d, J=8.2 Hz, 2H), 7.31 (t, J=1.8 Hz, 2H), 7.37-7.42 (m, 4H), 7.69 (d, J=8.2 Hz, 2H), 7.77-7.81 (m, 4H), 8.37 (d, J=9.2 Hz, 2H), 8.52 (d, J=9.2 Hz, 2H), 9.31 (d, J=9.2 Hz, 2H)

MALDI-TOF MS: m/z 1229 ([M+H]$^+$)

Anal. Calcd for C$_{73}$H$_{67}$IrN$_2$O$_4$: C, 71.37; H, 5.50; N, 2.28. Found: C, 71.74; H, 5.84; N, 2.13

Synthesis of Iridium Complex (1-B)

According to the following Formula, the iridium complex 1-B was obtained by reacting the precursor (1) and the β-diketone (B) with each other.

[Chemical Formula 22]

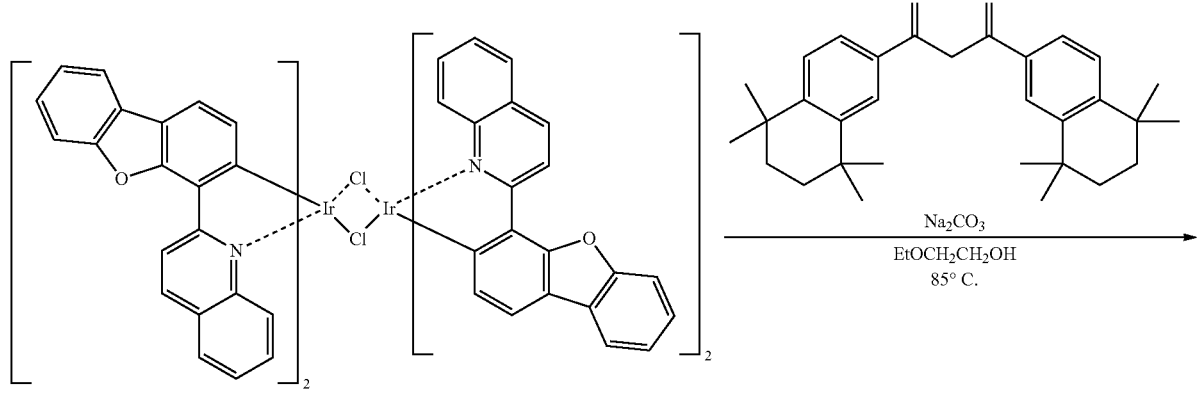

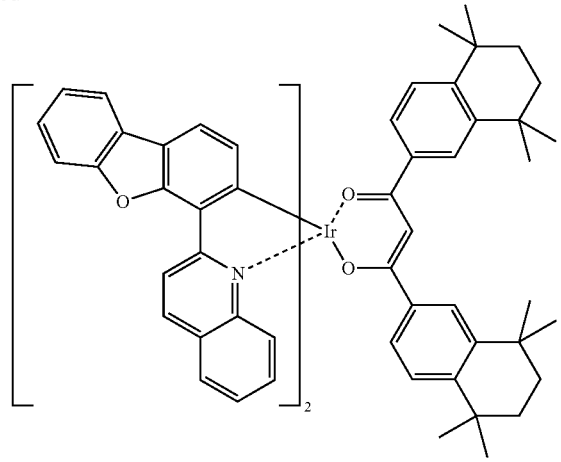

The precursor (1) (0.981 g, 0.601 mmol), 1,3-bis(5,5,8,8-tetramethyl-5,6,7,8-tetrahydronaphtalene-2-yl)propane-1,3-dione (0.537 g, 1.21 mmol) and sodium carbonate (0.796 g, 7.51 mmol) was added to 2-ethoxyethanol (200 mL), and the resulting mixture was stirred for 2 hours at 85° C. under a nitrogen atmosphere. After being allowed to cool, the solvent was distilled off under a reduced pressure, and then chloroform was added to the residue. The obtained mixed solution was washed with water and a saturated saline, and was then dried by adding an appropriate amount of sodium sulfate. After removal of the sodium sulfate by filtration, the solvent of the filtrate was distilled off with an evaporator. The iridium complex 1-B was obtained in a yield of 29% (426 mg, 0.348 mmol) by purifying the obtained residue with an alumina column chromatography (development solvent; chloroform:hexane=1:1.6 (v/v)), and by further performing recrystallization using chloroform-methanol.

$^1$H NMR (CDCl$_3$): δ1.08 (s, 6H), 1.10 (s, 6H), 1.16 (s, 6H), 1.18 (s, 6H), 1.57 (m, 8H), 5.79 (s, 1H), 6.65 (d, J=8.2 Hz, 2H), 7.09 (d, J=8.2 Hz, 2H), 7.13-7.18 (m, 4H), 7.21-7.29 (m, 6H), 7.34-7.43 (m, 4H), 7.69 (d, J=8.2 Hz, 2H), 7.77-7.79 (m, 4H), 8.34 (d, J=8.3 Hz, 2H), 8.50 (d, J=8.3 Hz, 2H), 9.29 (d, J=8.2 Hz, 2H)

MALDI-TOF MS: m/z 1225 ([M+H]$^+$)

Anal. Calcd for C$_{73}$H$_{63}$IrN$_2$O$_4$: C, 71.60; H, 5.19; N, 2.29. Found: C, 71.72; H, 5.52; N, 2.15

Synthesis of Iridium Complex (1-X)

According to the following Formula, the iridium complex 1-X was obtained by reacting the precursor (1) and the β-diketone (X) with each other.

[Chemical Formula 23]

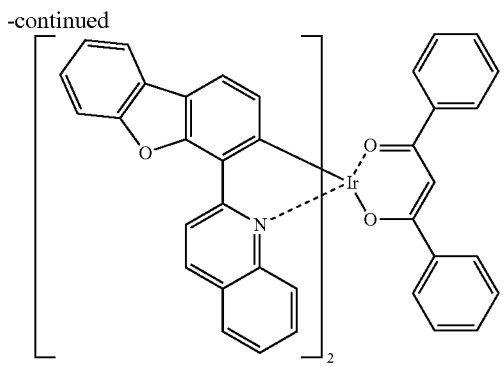

The precursor (1) (0.534 g, 0.327 mmol), 1,3-diphenyl-propane-1,3-dione (0.138 g, 0.615 mmol) and sodium carbonate (0.394 g, 3.72 mmol) was added to 2-ethoxyethanol (100 mL), and the resulting mixture was stirred for 2 hours at 85° C. under a nitrogen atmosphere. After being allowed to cool, the solvent was distilled off under a reduced pressure, and then chloroform was added to the residue. The obtained mixture was washed with water and a saturated saline, and was then dried by adding an appropriate amount of sodium sulfate. After removal of the sodium sulfate by filtration, the solvent of the filtrate was distilled off with an evaporator. The iridium complex 1-X was obtained in a yield of 1.6% (10.0 mg, 0.00996 mmol) by purifying the obtained residue with an alumina column chromatography (development solvent; chloroform:hexane=1:3), and by further performing recrystallization in chloroform-methanol. The properties of the thus synthesized compound were as follows.

$^1$H NMR (CDCl$_3$): δ5.94 (s, 1H), 6.64 (d, J=8.2 Hz, 2H), 7.12-7.23 (m, 8H), 7.28-7.30 (m, 4H), 7.35 (t, J=7.8 Hz, 2H), 7.41 (t, J=7.8 Hz, 2H), 7.48 (d, J=7.3 Hz, 4H), 7.70 (d, J=8.2 Hz, 2H), 7.77-7.80 (m, 4H), 8.32 (d, J=8.2 Hz, 2H), 8.50 (d, J=8.7 Hz, 2H), 9.26 (d, J=8.7 Hz, 2H)

MALDI-TOF MS: m/z 1004 (M$^+$)

Synthesis of Iridium Complex (2-A)

According to the following Formula, the iridium complex 2-A was obtained by reacting the precursor (2) and the β-diketone (A) with each other.

[Chemical Formula 24]

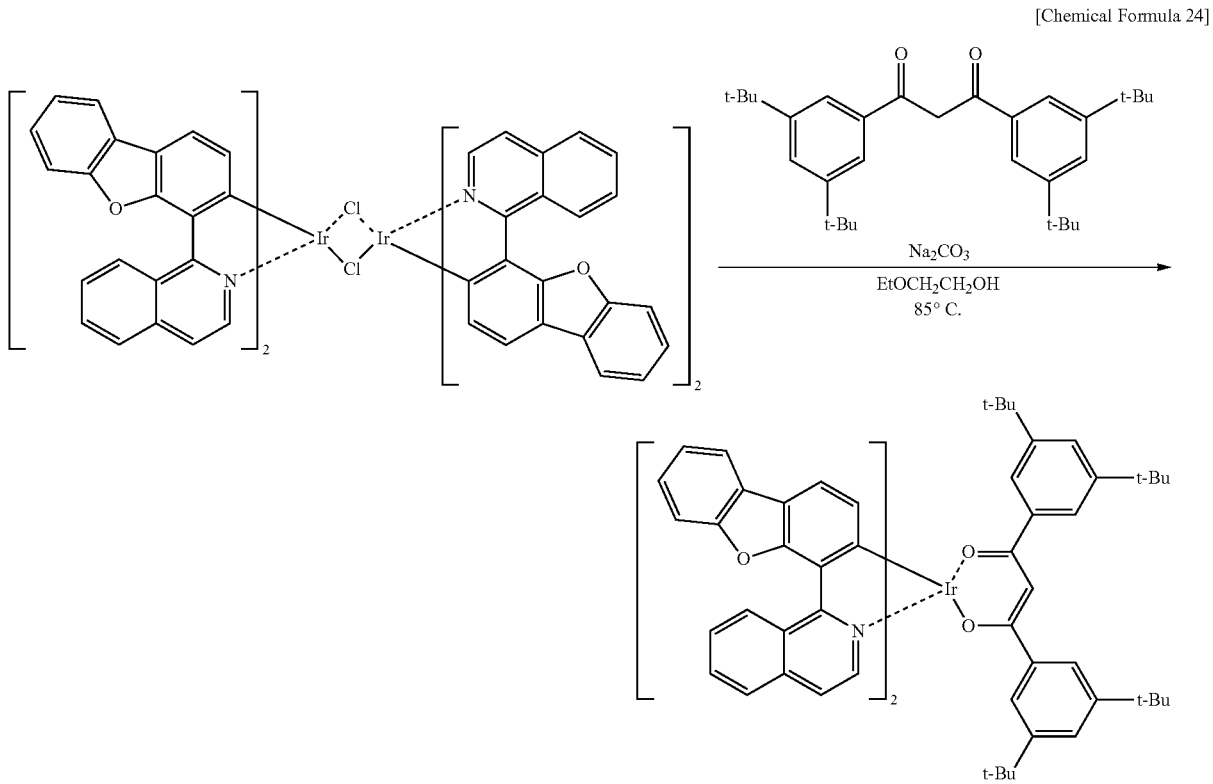

The precursor (2) (0.484 g, 0.296 mmol), 1,3-bis(3,5-di-tert-butyl phenyl)propane-1,3-dione (0.249 g, 0.555 mmol) and sodium carbonate (0.396 g, 3.74 mmol) was added to 2-ethoxyethanol (100 mL), and the resulting mixture was stirred for 2 hours at 85° C. under a nitrogen atmosphere. After being allowed to cool, the solvent was distilled off under a reduced pressure, and then chloroform was added to the residue. The obtained mixture was washed with water and a saturated saline, and was then dried by adding an appropriate amount of sodium sulfate. After removal of the sodium sulfate by filtration, the solvent of the filtrate was distilled off with an evaporator. The iridium complex 2-A was obtained in a yield of 9.0% (61.4 mg, 0.0500 mmol) by purifying the obtained residue with an alumina column chromatography (development solvent; chloroform: hexane=1:2), and by further performing recrystallization using chloroform-methanol. The properties of the thus synthesized compound were as follows.

$^1$H NMR (CDCl$_3$): δ1.08 (s, 36H), 6.42 (s, 1H), 6.60 (d, J=8.7 Hz, 2H), 7.22-7.26 (m, 2H), 7.30-7.34 (m, 10H), 7.36 (t, J=1.8 Hz, 2H), 7.49-7.52 (m, 2H), 7.71-7.79 (m, 6H), 7.90 (d, J=8.7 Hz, 2H), 8.61 (d, J=6.4 Hz, 2H), 9.18 (d, J=8.7 Hz, 2H)

MALDI-TOF MS: 1228 (M$^+$)

Anal. Calcd for C$_{73}$H$_{67}$IrN$_2$O$_4$: C, 71.37; H, 5.50; N, 2.28. Found: C, 71.21; H, 5.72; N, 2.04

Synthesis of Iridium Complex (2-B)

According to the following Formula, the iridium complex 2-B was obtained by reacting the precursor (2) and the β-diketone (B) with each other.

[Chemical Formula 25]

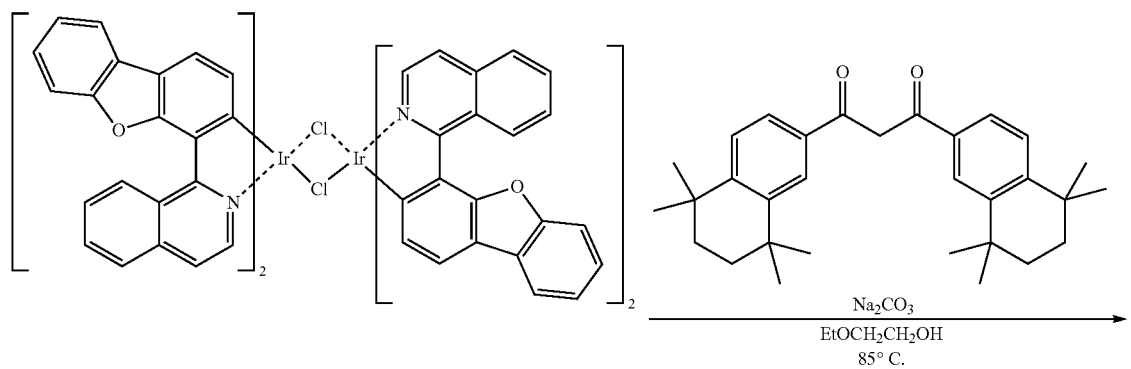

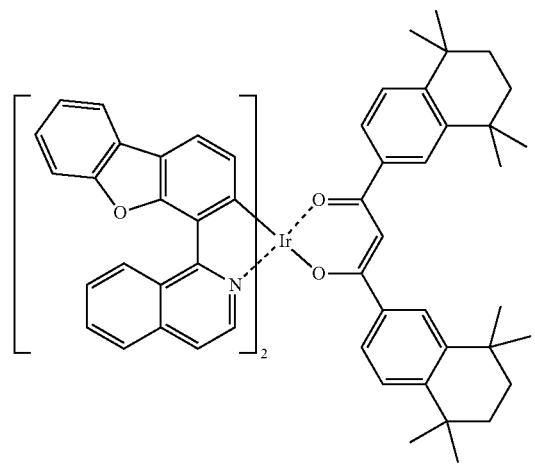

The precursor (1) (0.985 g, 0.603 mmol), 1,3-bis(5,5,8,8-tetramethyl-5,6,7,8-tetrahydronaphtalene-2-yl)propane-1,3-dione (0.532 g, 1.20 mmol) and sodium carbonate (0.791 g, 7.46 mmol) was added to 2-ethoxyethanol (200 mL), and the resulting mixture was stirred for 2 hours at 85° C. under a nitrogen atmosphere. After being allowed to cool, the solvent was distilled off under a reduced pressure, and then chloroform was added to the residue. The obtained mixed solution was washed with water and a saturated saline, and was then dried by adding an appropriate amount of sodium sulfate. After removal of the sodium sulfate by filtration, the solvent of the filtrate was distilled off with an evaporator. The iridium complex 2-B was obtained in a yield of 39% (573 mg, 0.468 mmol) by purifying the obtained residue with an alumina column chromatography (development solvent; chloroform:hexane=1:2 (v/v)), and by further performing recrystallization using chloroform-methanol.

$^1$H NMR (CDCl$_3$): δ1.08 (s, 6H), 1.15 (s, 6H), 1.16 (s, 6H), 1.18 (s, 6H), 1.57 (m, 8H), 6.47 (s, 1H), 6.49 (d, J=1.8 Hz, 2H), 7.13 (d, J=8.2 Hz, 2H), 7.32-7.36 (m, 4H), 7.41 (dd, J=1.8 and 8.2 Hz, 2H), 7.49-7.54 (m, 6H), 7.71-7.79 (m, 6H), 7.90-7.93 (m, 4H), 8.59 (d, J=6.4 Hz, 2H), 9.15 (d, J=8.2 Hz, 2H)

MALDI-TOF MS: m/z 1224 (M$^+$)

Anal. Calcd for C$_{73}$H$_{63}$IrN$_2$O$_4$: C, 71.60; H, 5.19; N, 2.29. Found: C, 71.72; H, 5.45; N, 2.11

Synthesis of Iridium Complex (2-X)

According to the following Formula, the iridium complex 2-X was obtained by reacting the precursor (2) and the β-diketone (X) with each other.

[Chemical Formula 26]

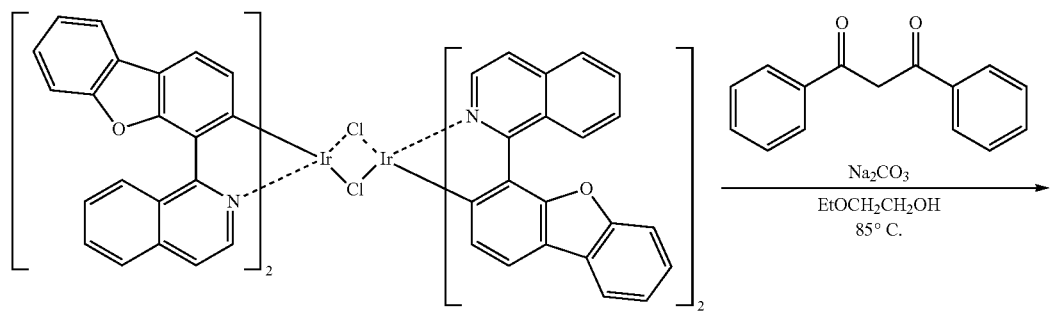

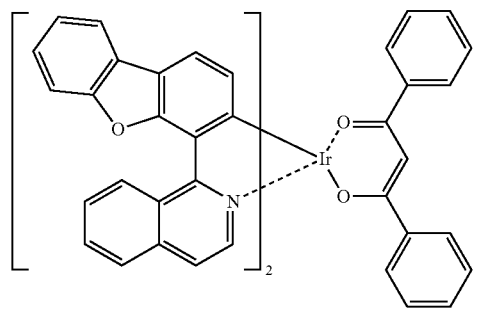

The precursor (2) (0.979 g, 0.600 mmol), 1,3-diphenyl-propane-1,3-dione (0.270 g, 1.20 mmol) and sodium carbonate (0.788 g, 7.43 mmol) was added to 2-ethoxyethanol (200 mL), and the resulting mixture was stirred for 2 hours at 85° C. under a nitrogen atmosphere. After being allowed to cool, the solvent was distilled off under a reduced pressure, and then chloroform was added to the residue. The obtained mixture was washed with water and a saturated saline, and was then dried by adding an appropriate amount of sodium sulfate. After removal of the sodium sulfate by filtration, the solvent of the filtrate was distilled off with an evaporator. The iridium complex 1-X was obtained in a yield of 5.7% (68.7 mg, 0.0684 mmol) by purifying the obtained residue with an alumina column chromatography (development solvent; chloroform), and by further performing recrystallization using chloroform-methanol. The properties of the thus synthesized compound were as follows.

$^1$H NMR (CDCl$_3$): δ6.44 (d, J=8.2 Hz, 2H), 6.57 (s, 1H), 7.18-7.24 (m, 4H), 7.30-7.38 (m, 8H), 7.50 (d, J=8.2 Hz, 2H), 7.53 (d, J=6.4 Hz, 2H), 7.69 (dd, J=1.3 and 8.2 Hz, 4H), 7.71-7.79 (m, 6H), 7.91 (d, J=8.2 Hz, 2H), 8.58 (d, J=6.4 Hz, 2H), 9.15 (d, J=8.2 Hz, 2H)

MALDI-TOF MS: 1004 (M$^+$)

Synthesis of Iridium Complex (3-A)

According to the following Formula, the iridium complex 3-A was obtained by reacting the precursor (3) and the β-diketone (A) with each other.

[Chemical Formula 27]

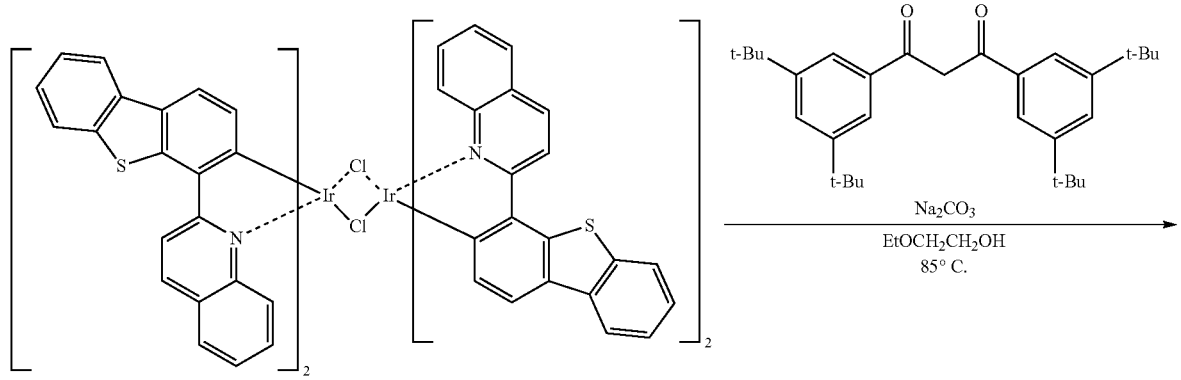

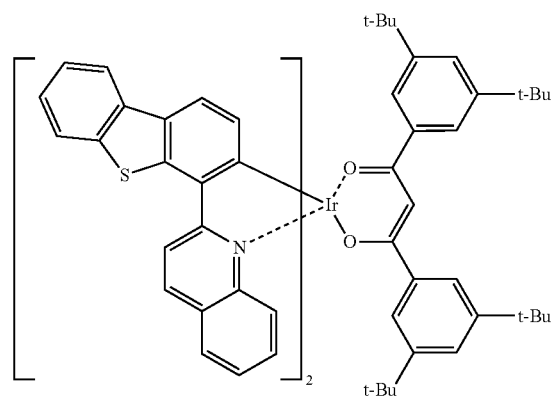

The precursor (3) (1.02 g, 0.601 mmol), 1,3-bis(3,5-di-tert-butyl phenyl)propane-1,3-dione (0.536 g, 1.19 mmol) and sodium carbonate (0.790 g, 7.45 mmol) was added to 2-ethoxyethanol (200 mL), and the resulting mixture was stirred for 2 hours at 85° C. under a nitrogen atmosphere. After being allowed to cool, the solvent was distilled off under a reduced pressure, and then chloroform was added to the residue. The obtained mixed solution was washed with water and a saturated saline, and was then dried by adding an appropriate amount of sodium sulfate. After removal of the sodium sulfate by filtration, the solvent of the filtrate was distilled off with an evaporator. The iridium complex 3-A was obtained in a yield of 32% (488 mg, 0.387 mmol) by purifying the obtained residue with an alumina column chromatography (development solvent; chloroform:hexane=1.6:1 (v/v)), and by further performing recrystallization using chloroform-methanol.

$^1$H NMR (CDCl$_3$): δ1.18 (s, 36H), 5.68 (s, 1H), 6.87 (d, J=8.2 Hz, 2H), 7.01 (d, J=1.8 Hz, 4H), 7.19 (dt, J=1.4 and 8.2 Hz, 2H), 7.31 (t, J=1.8 Hz, 2H), 7.35-7.41 (m, 6H), 7.46 (d, J=8.2 Hz, 2H), 7.81 (d, J=6.8 Hz, 2H), 7.92 (dd, J=1.4 and 8.2 Hz, 2H), 7.97 (dd, J=1.4 and 6.9 Hz, 2H), 8.43 (d, J=8.7 Hz, 2H), 8.46 (d, J=8.7 Hz, 2H), 8.83 (d, J=8.7 Hz, 2H)

MALDI-TOF MS: m/z 1260(M$^+$)

Anal. Calcd for C$_{73}$H$_{67}$IrN$_2$O$_2$S$_2$: C, 69.55; H, 5.36; N, 2.22. Found: C, 69.55; H, 5.36; N, 2.54

Synthesis of Iridium Complex (3-B)

According to the following Formula, the iridium complex 3-B was obtained by reacting the precursor (3) and the β-diketone (B) with each other.

[Chemical Formula 28]

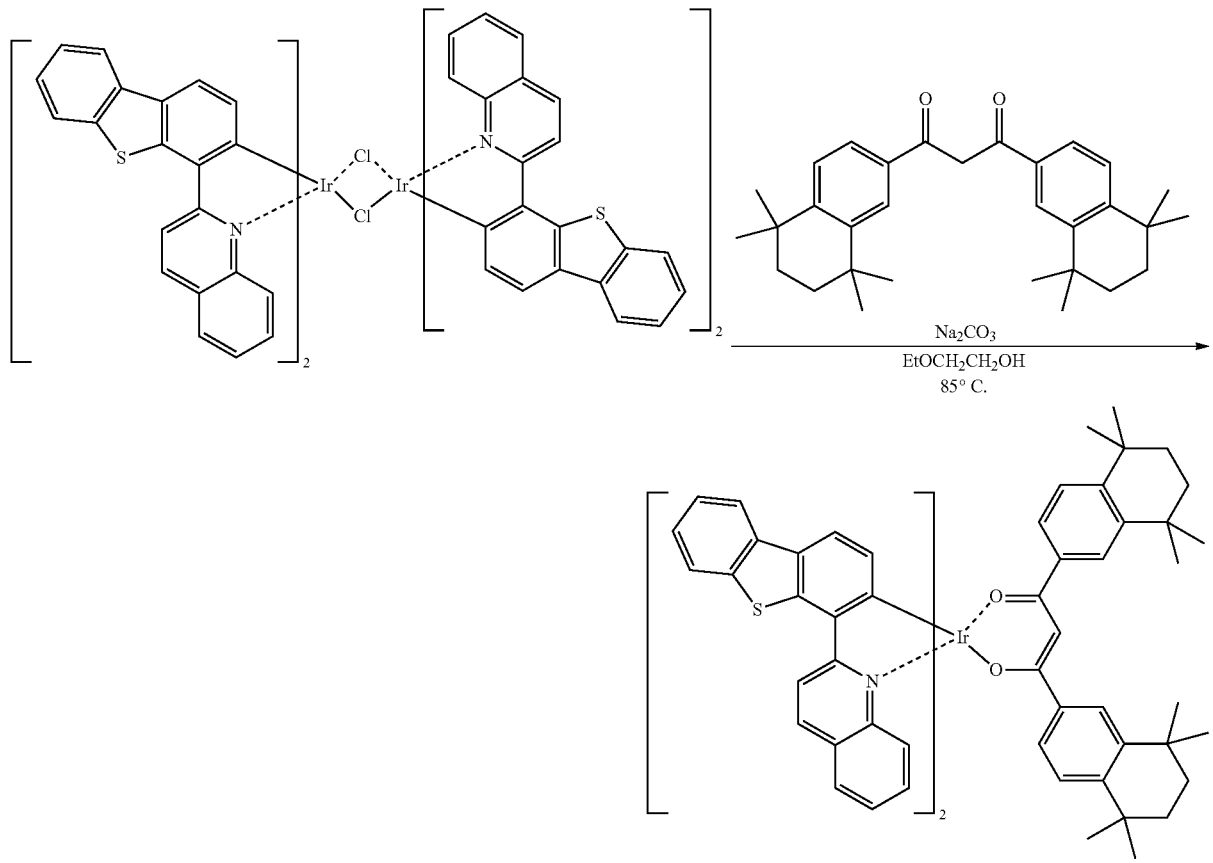

The precursor (3) (1.02 g, 0.601 mmol), 1,3-bis(5,5,8,8-tetramethyl-5,6,7,8-tetrahydronaphtalene-2-yl)propane-1,3-dione (0.532 g, 1.20 mmol) and sodium carbonate (0.787 g, 7.43 mmol) was added to 2-ethoxyethanol (200 mL), and the resulting mixture was stirred for 2 hours at 85° C. under a nitrogen atmosphere. After being allowed to cool, the solvent was distilled off under a reduced pressure, and then chloroform was added to the residue. The obtained mixed solution was washed with water and a saturated saline, and was then dried by adding an appropriate amount of sodium sulfate. After removal of the sodium sulfate by filtration, the solvent of the filtrate was distilled off with an evaporator. The iridium complex 3-B was obtained in a yield of 37% (558 mg, 0.444 mmol) by purifying the obtained residue with an alumina column chromatography (development solvent; chloroform:hexane=1:1.6 (v/v)), and by further performing recrystallization using chloroform-methanol.

$^1$H NMR (CDCl$_3$): δ1.08 (s, 6H), 1.10 (s, 6H), 1.16 (s, 6H), 1.18 (s, 6H), 1.57 (m, 8H), 5.80 (s, 1H), 6.65 (d, J=8.2 Hz, 2H), 7.09 (d, J=8.2 Hz, 2H), 7.13-7.16 (m, 4H), 7.18-7.30 (m,6H), 7.34-7.42 (m, 4H), 7.69 (d, J=8.2 Hz, 2H), 7.77-7.90 (m, 4H), 8.34 (d, J=8.7 Hz, 2H), 8.50 (d, J=8.7 Hz, 2H), 9.29 (d, J=8.7 Hz, 2H)

MALDI-TOF MS: m/z 1256 (M$^+$)

Anal. Calcd for C$_{73}$H$_{63}$IrN$_2$O$_2$S$_2$: C, 69.77; H, 5.05; N, 2.23. Found: C, 69.49; H, 5.25; N, 2.54

Synthesis of Iridium Complex (3-X)

According to the following Formula, the iridium complex 3-X was obtained by reacting the precursor (3) and the β-diketone (X) with each other.

[Chemical Formula 29]

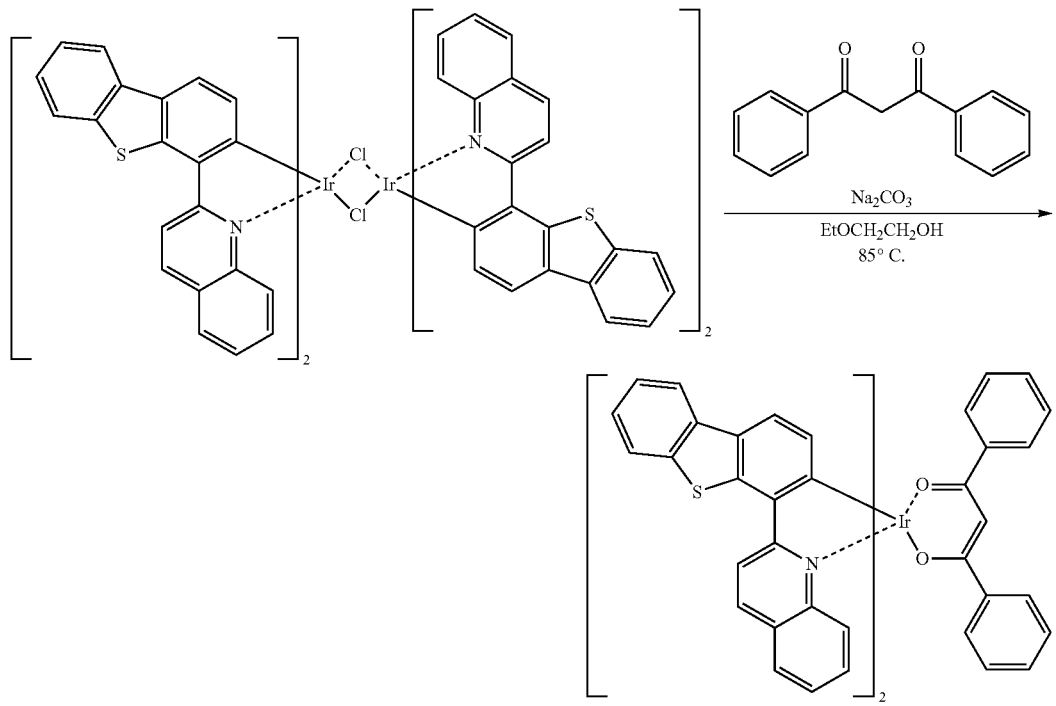

The precursor (3) (0.768 g, 0.453 mmol), 1,3-diphenylpropane-1,3-dione (0.271 g, 1.21 mmol) and sodium carbonate (0.592 g, 5.59 mmol) was added to 2-etoxyethanol (150 mL), and the resulting mixture was stirred for 2 hours at 85° C. under a nitrogen atmosphere. After being allowed to cool, the solvent was distilled off under a reduced pressure, and then chloroform was added to the residue. The obtained mixed solution was washed with water and a saturated saline, and was then dried by adding an appropriate amount of sodium sulfate. After removal of the sodium sulfate by filtration, the solvent of the filtrate was distilled off with an evaporator. The iridium complex 3-X was obtained in a yield of 5.7% (53.8 mg, 0.0519 mmol) by purifying the obtained residue with an alumina column chromatography (development solvent; chloroform: hexane=2:1 (v/v)), and by further performing recrystallization using chloroform-methanol.

$^1$H NMR (CDCl$_3$): δ5.87 (s, 1H), 6.85 (d, J=8.2 Hz, 2H), 7.10-7.20 (m, 6H), 7.32-7.51 (m, 14H), 7.78 (dd, 1.8 and 8.2 Hz, 2H), 7.92 (dd, J=1.4 and 6.9 Hz, 2H), 7.99 (dd, J=1.4 and 6.9 Hz, 2H), 8.36 (d, J=8.7 Hz, 2H), 8.44 (d, J=8.7 Hz, 2H), 8.74 (d, J=8.7 Hz, 2H)

MALDI-TOF MS: m/z 1036 (M$^+$)

Anal. Calcd for C$_{57}$H$_{35}$IrN$_2$O$_2$S$_2$: C, 66.07; H, 3.40; N, 2.70. Found: C, 66.20; H, 3.51; N, 2.61

Synthesis of Iridium Complex (4-A)

According to the following Formula, the iridium complex 4-A was obtained by reacting the precursor (4) and the β-diketone (A) with each other.

[Chemical Formula 30]

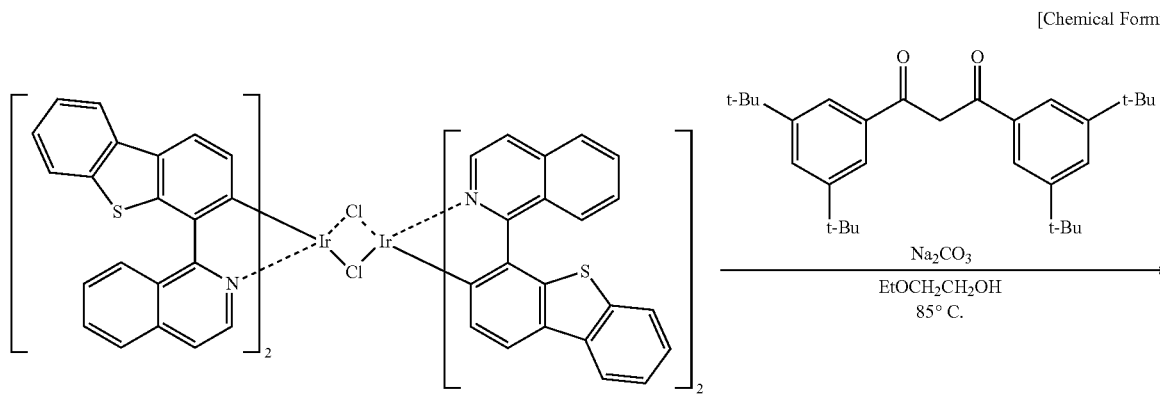

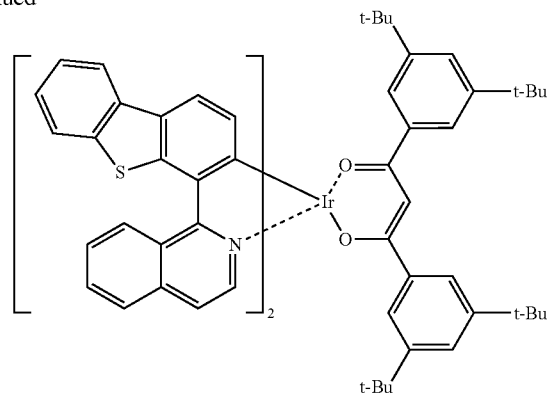

The precursor (4) (0.548 g, 0.323 mmol), 1,3-bis(3,5-di-tert-butyl phenyl)propane-1,3-dione (0.296 g, 0.660 mmol) and sodium carbonate (0.454 g, 4.28 mmol) was added to 2-ethoxyethanol (100 mL), and the resulting mixture was stirred for 2 hours at 85° C. under a nitrogen atmosphere. After being allowed to cool, the solvent was distilled off under a reduced pressure, and then chloroform was added to the residue. The obtained mixed solution was washed with water and a saturated saline, and was then dried by adding an appropriate amount of sodium sulfate. After removal of the sodium sulfate by filtration, the solvent of the filtrate was distilled off with an evaporator. The iridium complex 4-A was obtained in a yield of 29% (234 mg, 0.186 mmol) by purifying the residue with an alumina column chromatography (development solvent; chloroform:hexane=1:1 (v/v)), and by further performing recrystallization using chloroform-methanol.

$^1$H NMR (CDCl$_3$): δ1.07 (s, 36H), 6.41 (s, 1H), 6.59 (d, J=8.2 Hz, 2H), 7.22-7.26 (m, 2H) 7.29 (d, J=1.8 Hz, 4H), 7.31-7.35 (m, 6H), 7.49-7.52 (m, 4H), 7.71-7.77 (m, 6H), 7.90 (d, J=8.2 Hz, 2H), 8.61 (d, J=5.9 Hz, 2H), 9.18 (d, J=8.2 Hz, 2H)

MALDI-TOF MS: m/z 1261 ([M+H]$^+$)

Anal. Calcd for C$_{73}$H$_{67}$IrN$_2$O$_2$S$_2$: C, 69.55; H, 5.36; N, 2.22. Found: C, 69.38; H, 5.33; N, 2.37

Synthesis of Iridium Complex (4-B)

According to the following Formula, the iridium complex 4-B was obtained by reacting the precursor (4) and the β-diketone (B) with each other.

[Chemical Formula 31]

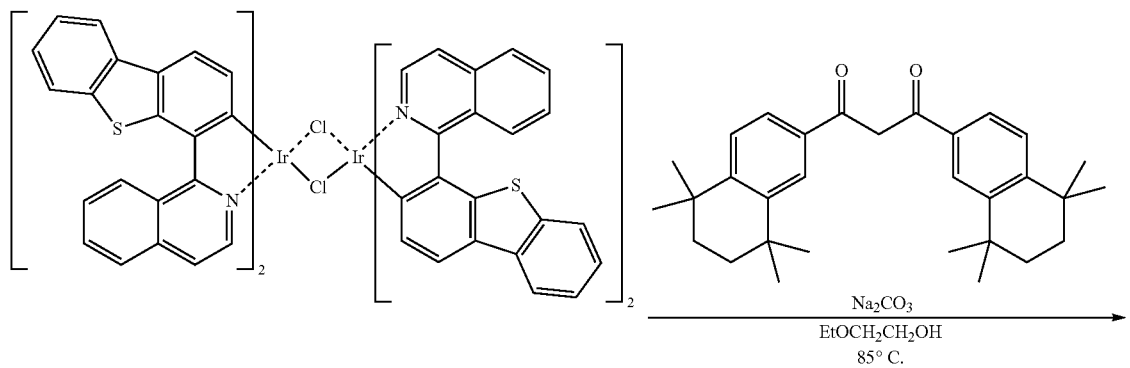

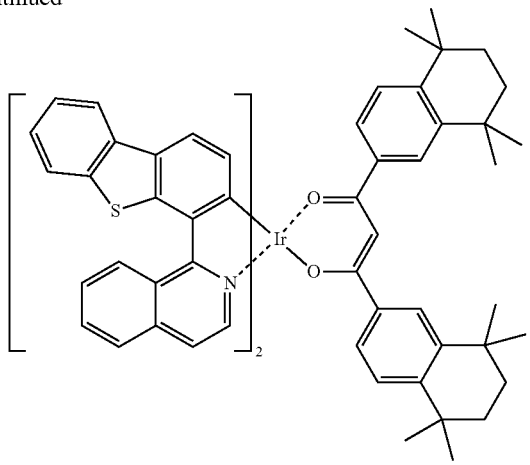

The precursor (4) (1.02 g, 0.601 mmol), 1,3-bis(5,5,8,8-tetramethyl-5,6,7,8-tetrahydronaphtalene-2-yl)propane-1,3-dione (0.532 g, 1.20 mmol) and sodium carbonate (0.789 g, 7.44 mmol) was added to 2-ethoxyethanol (200 mL), and the resulting mixture was stirred for 2 hours at 85° C. under a nitrogen atmosphere. After being allowed to cool, the solvent was distilled off under a reduced pressure, and then chloroform was added to the residue. The obtained mixed solution was washed with water and a saturated saline, and was then dried by adding an appropriate amount of sodium sulfate. After removal of the sodium sulfate by filtration, the solvent of the filtrate was distilled off with an evaporator.

The iridium complex 4-B was obtained in a yield of 26% (392 mg, 0.311 mmol) by purifying the obtained residue with an alumina column chromatography (development solvent; chloroform:hexane=1:2 (v/v)), and by further performing recrystallization using chloroform-methanol.

$^1$H NMR (CDCl$_3$): δ0.96 (s, 6H), 1.07 (s, 6H), 1.14 (s, 6H), 1.17 (s, 6H), 6.47 (d, J=7.7 Hz, 2H), 6.48 (s, 1H), 7.13 (d, J=8.2 Hz, 2H), 7.22-7.26 (m, 2H), 7.31-7.35 (m, 4H), 7.40 (dd, J=1.8 and 8.7 Hz, 2H), 7.49 (d, J=6.8 Hz,4H), 7.53 (d, J=1.8 Hz, 2H), 7.70-7.78 (m, 6H), 7.90 (d, J=7.7 Hz, 2H), 8.59 (d, J=6.8 Hz, 2H), 9.14 (d, J=8.7 Hz, 2H)

MALDI-TOF MS: m/z 1256 (M$^+$)

Anal. Calcd for C$_{73}$H$_{63}$IrN$_2$O$_2$S$_2$: C, 69.77; H, 5.05; N, 2.23. Found: C, 70.10; H, 5.31; N, 2.54

Synthesis of Iridium Complex (4-X)

According to the following Formula, the iridium complex 4-X was obtained by reacting the precursor (4) and the β-diketone with each other.

[Chemical Formula 32]

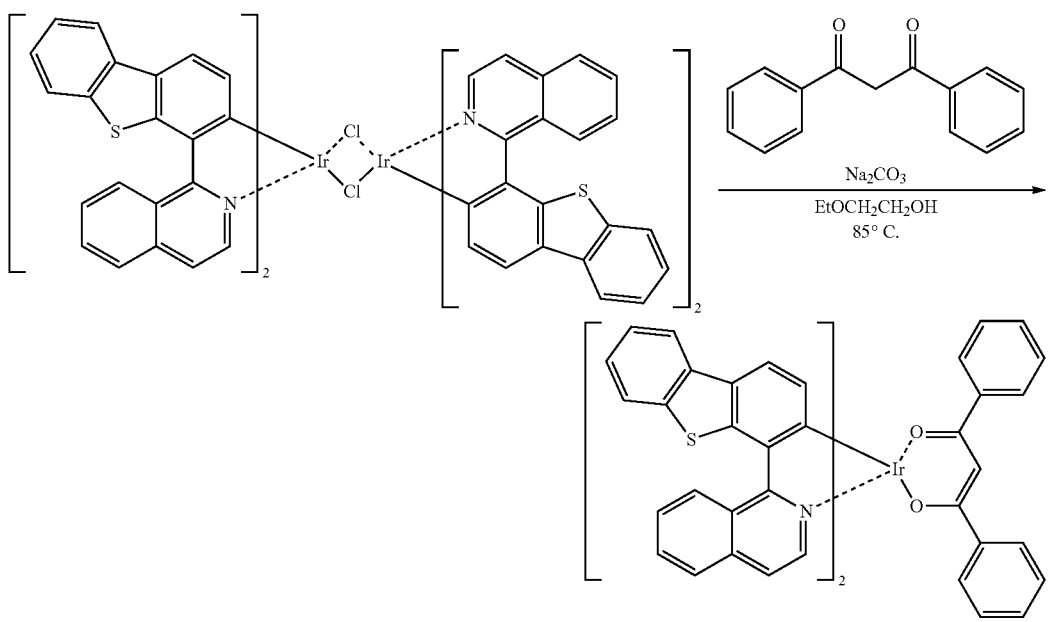

The precursor (4) (0.511 g, 0.301 mmol), 1,3-diphenyl-propane-1,3-dione (0.139 g, 0.620 mmol) and sodium carbonate (0.405 g, 3.82 mmol) was added to 2-etoxyethanol (100 mL), and the resulting mixture was stirred for 2 hours at 85° C. under a nitrogen atmosphere. After being allowed to cool, the solvent was distilled off under a reduced pressure, and then chloroform was added to the residue. The obtained mixed solution was washed with water and a saturated saline, and was then dried by adding an appropriate amount of sodium sulfate. After removal of the sodium sulfate by filtration, the solvent of the filtrate was distilled off with an evaporator. The iridium complex 4-X was obtained in a yield of 5.0% (31.1 mg, 0.0300 mmol) by purifying the obtained residue with an alumina column chromatography (development solvent; chloroform: hexane=1:1 (v/v)), and by further performing recrystallization using chloroform-methanol.

$^1$H NMR (CDCl$_3$): δ6.45 (d, J=7.7 Hz, 2H), 6.58 (s, 1H), 7.21 (t, J=7.6 Hz, 4H), 7.23-7.27 (m, 2H), 7.32-7.37 (m, 6H), 7.50 (d, J=8.2 Hz, 2H), 7.53 (d, J=6.4 Hz, 2H), 7.70 (d, J=7.6 Hz, 4H), 7.72-7.80 (m, 6H), 7.92 (dd, J=1.3 and 8.2 Hz, 2H), 8.59 (d, J=6.4 Hz, 2H), 9.16 (d, J=7.7 Hz, 2H)

MALDI-TOF MS: m/z 1036 (M$^+$)

Anal. Calcd for C$_{57}$H$_{35}$IrN$_2$O$_2$S$_2$: C, 66.07; H, 3.40; N, 2.70. Found: C, 66.07; H, 3.69; N, 2.70

The emission spectrum, the PL quantum yield and the thermal decomposition property of each iridium complex obtained above were evaluated. Furthermore, each organic EL element using each iridium complex was produced, and the properties were evaluated.

[Evaluation of Photoluminescence (PL) Spectrum and PL Quantum Yield]

The photoluminescence (PL) spectrum and the PL quantum yield $\phi_{PL}$ of each iridium complex obtained above were measured. Fluorolog-3 spectrometer manufactured by HORIBA, Ltd. was used for measuring the PL spectrum. C9920-12 Quantum yield measuring machine manufactured by HAMAMATSU Photonics K.K. was used for measuring the PL quantum yield. The evaluation of these PL spectrum and PL quantum yield were conducted both in an organic solvent (dichloromethane (CH$_2$Cl$_2$)) and in a polymer thin film (polymethyl methacrylate, PMMA), as medium. Note that the solution sample sealed with argon gas was measured as a deoxidized solution, and the polymer thin film sample was measured under a nitrogen atmosphere. The polymer thin film sample was measured by 4 wt % doping of each iridium complex into PMMA. The results are shown in the following Table.

TABLE 1

|  | In organic solvent | | In polymer thin film | |
| --- | --- | --- | --- | --- |
|  | $\lambda_{PL}$ (nm) | $\phi_{PL}$ | $\lambda_{PL}$ (nm) | $\phi_{PL}$ |
| 1-A | 610 | 0.42 | 603 | 0.47 |
| 1-B | 611 | 0.49 | 605 | 0.23 |
| 1-X | 609 | 0.17 | 603 | 0.34 |
| 2-A | 637 | 0.46 | 627 | 0.49 |
| 2-B | 642 | 0.32 | 637 | 0.27 |
| 2-X | 642 | 0.31 | 633 | 0.37 |
| 3-A | 618 | 0.66 | 612 | 0.61 |
| 3-B | 611 | 0.42 | 605 | 0.46 |
| 3-X | 615 | 0.39 | 612 | 0.43 |
| 4-A | 659 | 0.23 | 650 | 0.44 |
| 4-B | 659 | 0.22 | 651 | 0.25 |
| 4-X | 662 | 0.18 | 652 | 0.21 |

From the above Table 1, the iridium complex having the phenyl groups substituted by the β-diketone (A) or (B) is tend to have higher PL quantum yield $\phi_{PL}$ than the conventional iridium complexes (1-X, 2-X, 3-X, and 4-X) substituted by the β-diketone (X).

[Thermogravimetric Analysis (TG)]

The thermal decomposition property of the iridium complex was evaluated by the thermogravimetric analysis (TG). A weight change of a sample when 2 mg of the iridium complex was heated from about 50° C. to about 450° C. at an elevating rate of 10° C./min under a nitrogen stream (200 mL/min) was observed by using TG8120 thermogravimetric analysis machine manufactured by RIGAKU Corporation as the TG measuring machine. The results of measurement are shown in FIG. 1 and Table 2. The weight reduction percentage in Table 2 is defined as a weight reduction percentage relative to the initial weight.

TABLE 2

| | Temperature (° C.) that reaches each weight reduction percentage | | | | |
| --- | --- | --- | --- | --- | --- |
|  | 1% | 2% | 3% | 4% | 5% |
| 1-A | 306 | 344 | 383 | 401 | 407 |
| 1-B | 191 | 225 | 266 | 310 | 322 |
| 1-X | 144 | 164 | 194 | 251 | 313 |
| 2-A | 333 | 349 | 360 | 368 | 372 |
| 2-B | 261 | 269 | 278 | 284 | 289 |
| 2-X | 329 | 344 | 350 | 353 | 355 |
| 3-A | 276 | 303 | 329 | 364 | 391 |
| 3-B | 194 | 293 | 342 | 371 | 390 |
| 3-X | 286 | 329 | 359 | 373 | 378 |
| 4-A | 198 | 219 | 231 | 239 | 246 |
| 4-B | 323 | 334 | 340 | 347 | 352 |
| 4-X | 282 | 307 | 315 | 321 | 326 |

Figure 2:
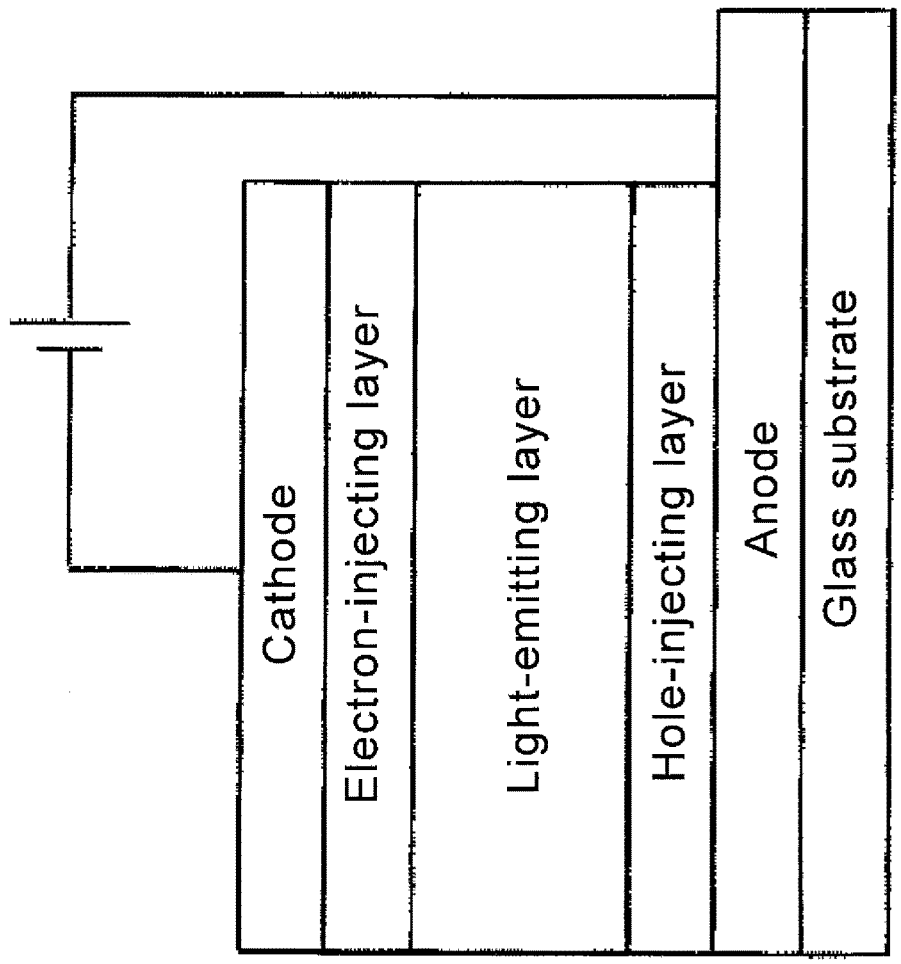
FIG. 2 is a cross-sectional schematic view of the organic EL element produced in the embodiment.

From the results of the above Table and FIG. 2, the iridium complex having the phenyl groups substituted by the β-diketone (A) or (B) is tend to have higher thermal stability than the conventional iridium complexes (1-X, 2-X, 3-X, and 4-X) substituted by the β-diketone (X).

[Production and Property Evaluation of Organic EL Element]

The organic EL element (1) shown in FIG. 2 was produced in the following procedures by using the iridium complexes 1-A, 2-A, 1-X and 2-X, and their properties were evaluated.

<Production of Organic EL Element>

(a) Formation of Hole-Infection Layer (5)

An anode (2) was prepared by subjecting an ITO-glass substrate (manufactured by SANYO Vacuum Industries Co., Ltd., ITO, film thickness 150 nm) to patterning treatment and then by performing washing. Next, the ITO thin film was surface-treated by ozone. After the surface treatment, a hole-injection layer (5) having a thickness of 40 nm was formed by rapid film formation of a hole injection material on the ITO film through the use of the spin coating method, and by baking at 120° C. for 1 hour. An electrically conductive polymer (P VP CH8000 manufactured by Heraeus Clevios) containing PEDOT and PSS was used as the hole injection material.

(b) Formation of Emission Layer (4)

An ink Ink(1-A) for the emission layer was prepared by dissolution of poly(9-vinylcarbasol) (PVCz, manufactured by Sigma-Aldrich, Number average molecular weight Mn, 25000-50000, purified by re-precipitating from THF-methanol), 2-(4-biphenilyl)-5-(4-tert-butylphenyl)-1,3,4-oxadiazole (PBD) and the iridium complex 1-A in a dehydrated toluene, and by filtration with a membrane filter (0.2 μm Millex-FG manufactured by Merck Millipore Corporation). The weight ratio among PVCz, PBD and iridium complex was 10:3.0:1.0, and 0.7 ml of the toluene relative to 10 mg of PVCz was used as a solvent for the ink. Through the use of the ink (1-A) for the obtained emission layer, an emission layer 4 having a thickness of 80 nm was formed on the hole-injection layer (5) by film formation using the spin coating method, and then by baking at 120° C. for 1 hour.

(c) Formation of Electron-Infection Layer (6) and Cathode (3)

A thin film of cesium fluoride (electron-injection layer (6), thickness 1 nm) as the electron injecting-material was formed by the vacuum deposition, through the use of a shadow mask, and then, a thin film of aluminum (cathode (3), thickness 250 nm) was produced. At this time, the electron-injection layer (6) and the cathode (3) were produced so that the area of the light-emitting area was 10 mm2 (2 mm×5 mm). In this way, the organic EL element EL(1-A) was completed.

<Production of Organic EL Element Used Each Iridium Complex as Light-Emitting Material>

Each ink for the emission layer was prepared by using each iridium complex (1-B, 1-X, 2-A, 2-B, 2-X, 3-A, 3-B, 3-X, 4-A, 4-B, and 4-X) instead of the iridium complex 1-A. Each organic EL element EL was obtained in the same way as in the above procedures except for using the ink Ink for the emission layer.

<Evaluation of Organic EL Element Properties>

Samples for evaluating the organic EL properties were produced by sealing the organic EL element obtained by the above steps into a cavity glass by using an ultraviolet curable resin.

The organic EL element properties such as EL spectrum, maximum luminance $L_{max}$ (cd/m$^2$), maximum external photoluminescence quantum efficiency $\eta_{ext.max}$ (%), and CIE standard colorimetric system (x,y) were measured by a luminance goniophotometer (C-9920-11, manufactured by HAMAMATSU Photonics K.K.).

Table 3 shows the results of the peak wavelength $\lambda_{EL}$ (nm), the maximum luminance $L_{max}$ (cd/m$^2$), the maximum external photoluminescence quantum efficiency $\eta_{ext.max}$ (%), the maximum current efficiency $\eta_{j,max}$ (cd/A), the maximum power efficiency $\eta_{p,max}$ (lm/W), and CIE standard colorimetric system (x,y). The $L_{max}$ and $\eta_{ext,max}$ are shown along with the applied voltage (V) at the time of measurement in brackets. Note that the luminescence starting voltage $V_{turn-on}$ represents the voltage at which the luminance reaches 1 cd/m$^2$.

Figure 3:
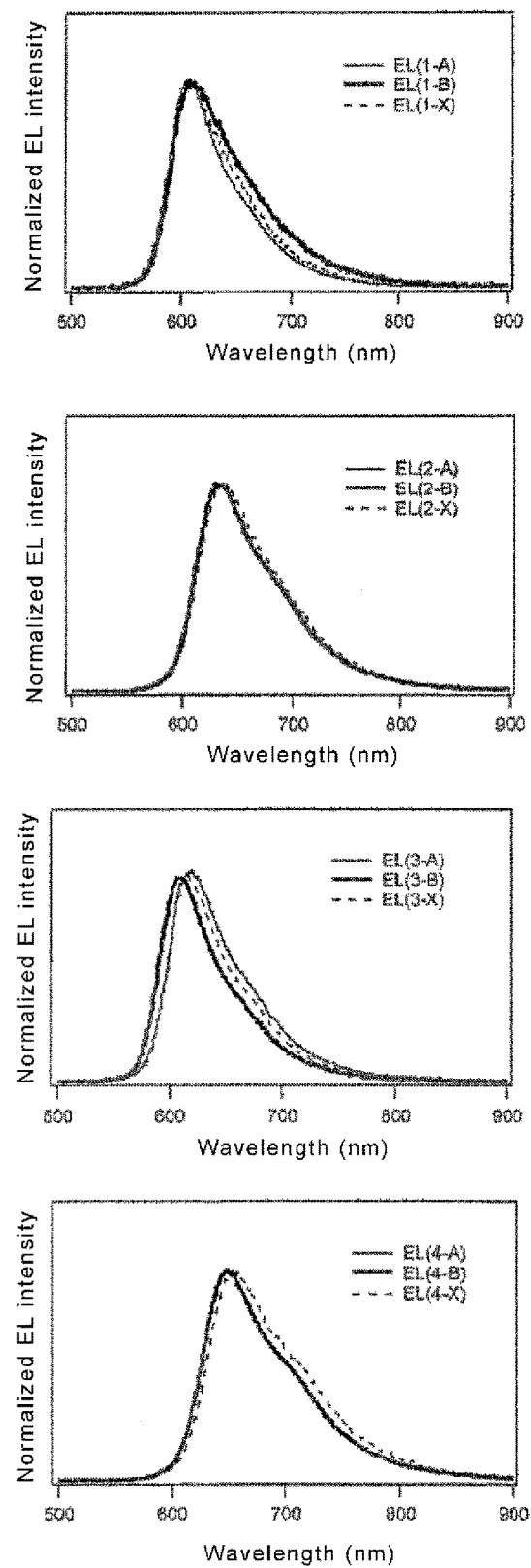
FIG. 3 shows the results of evaluating electroluminescent property of the organic EL element in which the organic iridium complex is used as a light-emitting material according to the embodiment.

Furthermore, FIG. 3 shows the electroluminescent (EL) spectrum of each organic EL element. The EL spectrum was measured at the maximum luminance $L_{max}$.

TABLE 3

| Element | Luminescence starting voltage $V_{turn-on}$/ V | Maximum luminance $L_{max}$/ cd m$^{-2}$ (@V) | Maximum external quantum efficiency $\eta_{ext.\,max}$/ % (@V) | Maximum current efficiency $\eta_{j,\,max}$/ cd A$^{-1}$ (@V) | Maximum power efficiency $\eta_{p,\,max}$/ lm W$^{-1}$ (@V) | $\lambda_{EL}$/ nm | CIE (x,y) |
|---|---|---|---|---|---|---|---|
| EL (1-A) | 5.5 | 3710 (18.0) | 2.13 (10.0) | 3.22 (10.0) | 1.22 (7.0) | 607 | (0.64, 0.36) |
| EL (1-B) | 8.5 | 670 (17.5) | 0.79 (12.0) | 0.98 (14) | 0.25 (12.0) | 609 | (0.64, 0.35) |
| EL (1-X) | 7 | 840 (18.0) | 0.47 (11.5) | 0.68 (10.5) | 0.21 (10.0) | 608 | (0.63, 0.37) |
| EL (2-A) | 7.5 | 2050 (20.5V) | 2.18 (12.5) | 1.4 (12.5) | 0.36 (12.0) | 638 | (0.68, 0.32) |
| EL (2-B) | 7 | 1610 (17.5) | 2.3 (12.5) | 1.49 (12.5) | 0.42 (10.0) | 638 | (0.68, 0.31) |
| EL (2-X) | 6 | 1250 (19.0) | 1.56 (12.0) | 0.89 (12.0) | 0.25 (11.0) | 639 | (0.68, 0.32) |
| EL (3-A) | 5 | 8950 (18.0) | 4.2 (8.5) | 5.39 (6.0) | 2.82 (6.0) | 616 | (0.66, 0.34) |
| EL (3-B) | 6.5 | 1900 (15.5) | 2.66 (11.5) | 3.87 (11.5) | 1.14 (10.0) | 607 | (0.64, 0.36) |
| EL (3-X) | 7 | 2830 (19.0) | 1.26 (12.0) | 1.36 (12.5) | 0.41 (10.0) | 620 | (0.66, 0.34) |
| EL (4-A) | 7 | 1390 (16..0) | 2.71 (10.5) | 1.00 (10.0) | 0.32 (10.0) | 648 | (0.68, 0.30) |
| EL (4-B) | 6 | 1050 (16.0) | 1.75 (13.0) | 0.68 (13.0) | 0.19 (10.5) | 649 | (0.68, 0.30) |
| EL (4-X) | 7 | 880 (17.0) | 1.22 (13.5) | 0.36 (13.5) | 0.09 (11.0) | 654 | (0.70, 0.30) |

From the above results, the organic EL elements produced by using complexes 1-A, 1-B, 2-A, 2-B, 3-A, 3-B, 4-A, and 4-B exhibit organic EL properties equal to or more than those of the EL produced by using the complexes 1-X, 2-X, 3-X, and 4-X.

INDUSTRIAL APPLICABILITY

The organic iridium complex of the present invention is suitable as the light-emitting material of the organic EL element because of its high quantum efficiency. In addition, the complex has high heat resistance and contributes to lifetime prolongation of the organic EL element.

The invention claimed is:
1. An organic iridium complex for an organic electroluminescent element represented by the following Formula

[Chemical Formula 1]

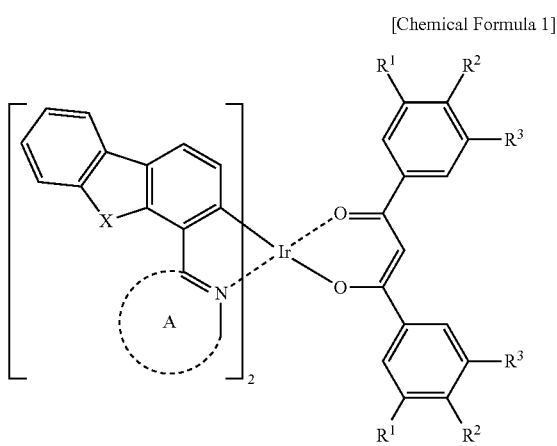

wherein $R^1$, $R^2$, and $R^3$ are each a tert-butyl group or a hydrogen atom, and the β-diketone ligand has at least one tert-butyl group; they may bond each other to thereby form a saturated hydrocarbon ring when the β-diketone ligand has two tert-butyl groups; A is a substituent having a heterocyclic ring which is either a 5-membered ring or a 6-membered ring and containing nitrogen; the heterocyclic ring of A is optionally fused to a benzene ring and may include sulfur atom (S) or oxygen atom (O) as a hetero atom other than nitrogen (N); X is a hetero atom.

2. The organic iridium complex according to claim 1, wherein
the β-diketone ligand is represented by any of the following Formula

[Chemical Formula 2]

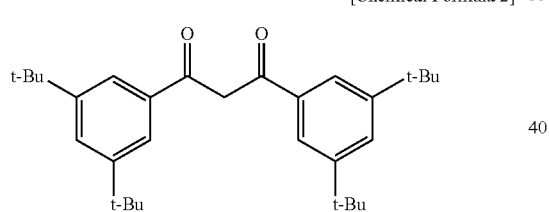

$R^1$ and $R^3$ are each a tert-butyl group, and $R^2$ is hydrogen,

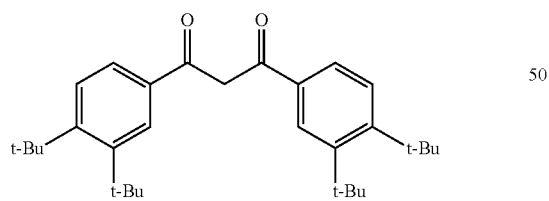

$R^2$ and $R^3$ are each a tert-butyl group, and $R^1$ is hydrogen,

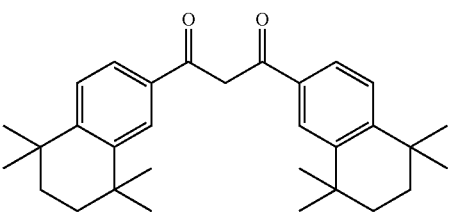

$R^2$ and $R^3$ are each a tert-butyl group, which bond each other to form a saturated hydrocarbon ring, and $R^1$ is hydrogen.

3. The organic iridium complex according to claim 1, wherein the A is a substituent composed of a condensed structure of the heterocyclic ring including nitrogen and a benzene ring.

4. The organic iridium complex according to claim 3, wherein the heterocyclic ring or the benzene ring of the A has a substituent containing fluorine or oxygen.

5. The organic iridium complex according to claims 1, wherein the heterocyclic ring of the A further includes sulfur atom (S) or oxygen atom (O) as the hetero atom.

6. The organic iridium complex according to claim 1, wherein the A is represented by any of the following Formula

[Chemical Formula 3]

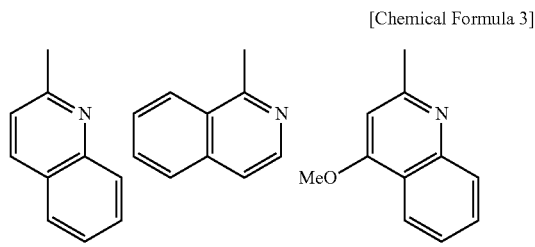

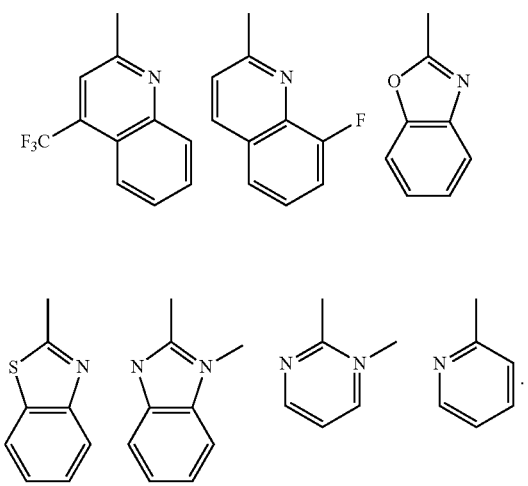

7. The organic iridium complex according to claim 1, wherein X is an oxygen atom (O) or a sulfur atom (S).

8. The organic iridium complex according to claim 1, wherein a PL quantum yield ΦPL when 4 wt % doping is performed in a polymer thin film is 0.4 or more.

9. An organic electroluminescent element including an emission layer having the organic iridium complex according to claim 1.

10. The organic iridium complex according to claim 1, wherein the A is a substituent composed of a condensed structure of the heterocyclic ring including nitrogen and a benzene ring.

11. The organic iridium complex according to claim 2, wherein the heterocyclic ring of the A further includes sulfur atom (S) or oxygen atom (O) as the hetero atom.

12. The organic iridium complex according to claim 2, wherein the A is represented by any of the following Formula

[Chemical Formula 3]

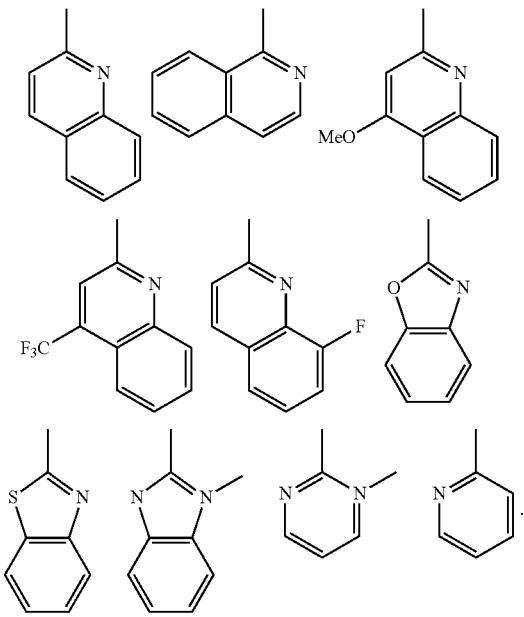

13. The organic iridium complex according to claim 2, wherein X is an oxygen atom (O) or a sulfur atom (S).

14. The organic iridium complex according to claim 2, wherein a PL quantum yield ΦPL 4 wt % doping is performed in a polymer thin film is 0.4 or more.

15. The organic iridium complex according to claim 3, wherein the heterocyclic ring of the A further includes sulfur atom (S) or oxygen atom (O) as the hetero atom.

16. The organic iridium complex according to claim 3, wherein the A is represented by any of the following Formula

[Chemical Formula 3]

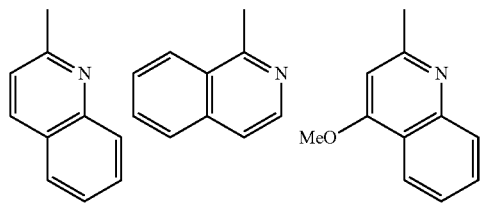
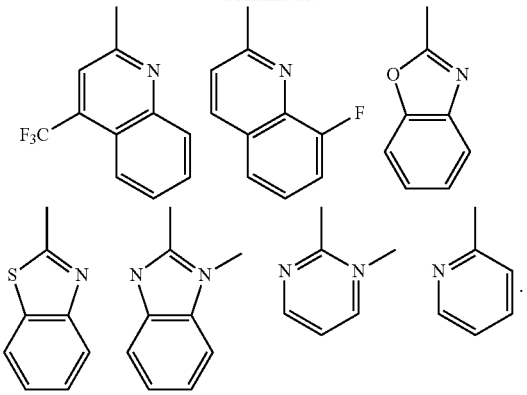

17. The organic iridium complex according to claim 3, wherein X is an oxygen atom (O) or a sulfur atom (S).

18. The organic iridium complex according to claim 3, wherein a PL quantum yield ΦPL when 4 wt % doping is performed in a polymer thin film is 0.4 or more.

19. The organic iridium complex according to claim 4, wherein the heterocyclic ring of the A further includes sulfur atom (S) or oxygen atom (O) as the hetero atom.

20. The organic iridium complex according to claim 4, wherein the A is represented by any of the following Formula

[Chemical Formula 3]

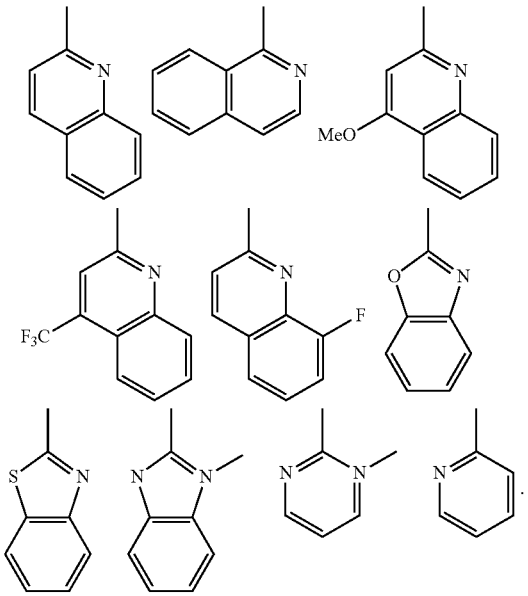

* * * * *